United States Patent
Markovic et al.

(10) Patent No.: US 11,427,637 B2
(45) Date of Patent: *Aug. 30, 2022

(54) METHODS OF TREATING PD-L1 EXPRESSING CANCER

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 359 days.

This patent is subject to a terminal disclaimer.

(21) Appl. No.: 16/330,360

(22) PCT Filed: Sep. 5, 2017

(86) PCT No.: PCT/US2017/050137
§ 371 (c)(1),
(2) Date: Mar. 4, 2019

(87) PCT Pub. No.: WO2018/048816
PCT Pub. Date: Mar. 15, 2018

(65) Prior Publication Data
US 2021/0130469 A1    May 6, 2021

Related U.S. Application Data

(60) Provisional application No. 62/383,938, filed on Sep. 6, 2016.

(51) Int. Cl.
| | | |
|---|---|---|
| *C07K 16/28* | (2006.01) | |
| *A61K 47/69* | (2017.01) | |
| *C07K 14/76* | (2006.01) | |
| *A61K 31/337* | (2006.01) | |
| *A61P 35/00* | (2006.01) | |
| *A61K 45/06* | (2006.01) | |

(52) U.S. Cl.
CPC ........ *C07K 16/2827* (2013.01); *A61K 31/337* (2013.01); *A61K 45/06* (2013.01); *A61K 47/6929* (2017.08); *A61P 35/00* (2018.01); *C07K 14/76* (2013.01)

(58) Field of Classification Search
CPC combination set(s) only.
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,533,058 B2 | 1/2017 | Markovic et al. |
| 9,555,128 B2 | 1/2017 | Markovic et al. |
| 9,566,350 B2 | 2/2017 | Markovic et al. |

(Continued)

FOREIGN PATENT DOCUMENTS

| | | |
|---|---|---|
| EP | 1913947 | 4/2008 |
| EP | 3204413 | 8/2017 |

(Continued)

OTHER PUBLICATIONS

Camidge et al (J of Thoracic Oncology, 2015, 10(sup 2), p. S176-S177, abstract ORAL 02.07).*
Giaccone et al (European J Cancer, 2015, 51 (Supp 3), p. S107-S108, abstract 513).*
Adams et al (J Clinical Oncology, May 2016, 34:No. 15 Suppl; abstract # 1009)(IDS).*
Brahmer et al (New England J Medicine, 2012, 366:26, p. 2455-2465).*
Foy et al (J Clinical Oncology, 2014, 32, No. 15, Suppl 3, abstract 3058).*
"Concurrent Infusions", J Oncol Pract., 4(4): 171, Jul. 2008.

(Continued)

*Primary Examiner* — Laura B Goddard
(74) *Attorney, Agent, or Firm* — Baker Botts L.L.P.

(57) ABSTRACT

Described herein are methods, formulations and kits for treating a patient with cancer with nanoparticle complexes comprising a carrier protein, a binding agent and paclitaxel and optionally co-treated with an anti-PD-L1 antibody.

7 Claims, 6 Drawing Sheets

(56) References Cited

U.S. PATENT DOCUMENTS

| | | |
|---|---|---|
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Swiss et al. |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,633 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Desai et al. |
| 2014/0161819 A1 | 6/2014 | Hann et al. |
| 2014/0178486 A1* | 6/2014 | Markovic ........ A61K 39/3955 424/499 |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic |
| 2017/0326234 A1* | 11/2017 | Renschler .......... A61K 45/06 |
| 2018/0155429 A1* | 6/2018 | Finckenstein ....... A61K 45/06 |
| 2018/0235886 A1 | 8/2018 | Markovic et al. |
| 2019/0022188 A1 | 1/2019 | Markovic |
| 2019/0038761 A1 | 2/2019 | Markovic et al. |
| 2019/0099498 A1 | 4/2019 | Markovic et al. |
| 2019/0184032 A1 | 6/2019 | Markovic et al. |
| 2019/0201546 A1 | 7/2019 | Markovic et al. |
| 2019/0202916 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |
| 2020/0308294 A1 | 10/2020 | Markovic |

FOREIGN PATENT DOCUMENTS

| | | |
|---|---|---|
| EP | 3533870 | 9/2019 |
| JP | S60146833 | 8/1985 |
| JP | S6178731 | 4/1986 |
| JP | H04504253 | 7/1992 |
| JP | 2001072589 | 3/2001 |
| JP | 2012522809 | 9/2012 |
| KR | 1020090078330 | 7/2009 |
| RU | 2011133819 | 2/2013 |
| RU | 2505315 C2 | 1/2014 |
| WO | 89/10398 | 11/1989 |
| WO | 97/49390 | 12/1997 |
| WO | 99/00113 | 1/1999 |
| WO | 99/51248 | 10/1999 |
| WO | 2012/048223 | 4/2002 |
| WO | 2004/022097 | 3/2004 |
| WO | 2004/096224 | 11/2004 |
| WO | 2006/034455 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | 2008/057562 | 5/2008 |
| WO | 2008076373 A1 | 6/2008 |
| WO | 2008/112987 | 9/2008 |
| WO | 2009/043159 | 4/2009 |
| WO | 2009/055343 | 4/2009 |
| WO | 2010/003057 | 1/2010 |
| WO | 2010/017216 | 2/2010 |
| WO | 2010/118365 | 10/2010 |
| WO | 2010/124009 | 10/2010 |
| WO | 2010/136492 | 12/2010 |
| WO | 2012/088388 | 6/2012 |
| WO | 2012/154681 | 11/2012 |

(56) References Cited

FOREIGN PATENT DOCUMENTS

| WO | 2012/154861 | 11/2012 |
|---|---|---|
| WO | 2014/009774 | 1/2014 |
| WO | 2014/037422 | 3/2014 |
| WO | 2014/055415 | 4/2014 |
| WO | 2014/105644 | 7/2014 |
| WO | 2014/123612 | 8/2014 |
| WO | 2015/048520 | 4/2015 |
| WO | 2015/095404 | 6/2015 |
| WO | 2015/173267 | 11/2015 |
| WO | 2015/191969 | 12/2015 |
| WO | 2015/195476 | 12/2015 |
| WO | 2016/057554 | 4/2016 |
| WO | 2016/059220 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048616 | 3/2018 |
| WO | 2018/048815 | 3/2018 |
| WO | 2018/048958 | 3/2018 |

OTHER PUBLICATIONS

Abraxane® for Injectable Suspension (paclitaxel protein-bound particles for injectable suspension) (alburnin-bound), [drug label], 22 pages, Sep. 2009.
Abraxis Bioscience, Inc., "Abraxane: For the adjuvant treatment of node-positive breast cancer administered sequentially to standard doxorubicin-containing combination chemotherapy," Oncologic Drugs Advisory Committee Meeting (available to public Aug. 4, 2006).
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(18S):8510 (Abstract).
Allen "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II, multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patents with unresectable stage IV melanoma", U.S. National Institutes of Health, 2007, 4 pages.
Anonymous, "Study of Bevacizumab With Carboplatin and Paclitaxel Chemotherapy for the First-Line Treatment of Patients With Metastastic Melanoma (BEAM)." ClinicalTrials.gov [online], Retrieved from the Internet: URL: https://clinicaltrials.gov/archive/NCT00434252/200703 12, dated Mar. 12, 2007, 3 pages.
U.S. Appl. No. 14/116,619, office action dated Feb. 4, 2015.
U.S. Appl. No. 14/116,619, office action dated Apr. 28, 2016.
U.S. Appl. No. 14/116,619, office action dated Sep. 10, 2015.
U.S. Appl. No. 14/432,979, office action dated Jan. 7, 2019.
U.S. Appl. No. 14/432,979, office action dated May 16, 2018.
U.S. Appl. No. 14/432,979, office action dated Jun. 30, 2016.
U.S. Appl. No. 14/432,979, ofiice action dated Oct. 4, 2017.
U.S. Appl. No. 14/432,979, office action dated Dec. 15, 2016.
U.S. Appl. No. 14/882,327, office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Aug. 16, 2018.
U.S. Appl. No. 15/030,568, office action dated Dec. 1, 2017.
U.S. Appl. No. 15/052,336, office action dated Jan. 22, 2019.
U.S. Appl. No. 15/052,336, office action dated Feb. 9, 2018.
U.S. Appl. No. 15/052,336, office action dated Sep. 4, 2018.
U.S. Appl. No. 15/052,623, office action dated Jan. 7, 2019.
U.S. Appl. No. 15/052,623, office action dated Feb. 9, 2018.
U.S. Appl. No. 15/052,623, office action dated May 19, 2017.
U.S. Appl. No. 15/652,623, office action dated Jul. 9, 2018.
U.S. Appl. No. 15/052,623, office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/092,433, office action dated Dec. 12, 2018.
U.S. Appl. No. 15/187,672, office action dated May 31, 2018.
U.S. Appl. No. 15/187,672, office action dated Nov. 28, 2018.
U.S. Appl. No. 15/187,672, office action dated Jan. 20, 2017.
U.S. Appl. No. 15/202,115, office action dated Sep. 26, 2016.
U.S. Appl. No. 15/225,428, office action dated Aug. 14, 2016.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16 2017.
U.S. Appl. No. 15/286,024, office action dated Jan. 6, 2017.
U.S. Appl. No. 15/286,024, office action dated May 19, 2017.
U.S. Appl. No. 15/331,754, office action dated Feb. 22, 2019.
U.S. Appl. No. 15/331,754, office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,536, office action dated Oct. 1, 2018.
U.S. Appl. No. 15/412,554, office action dated Sep. 27, 2018.
U.S. Appl. No. 15/412,564, office action dated Jul. 10, 2018.
U.S. Appl. No. 15/412,581; office action dated Nov. 13, 2018.
U.S. Appl. No. 15/412,596, office action dated Sep. 4, 2018.
U.S. Appl. No. 15/412,596, dated Dec. 27, 2018.
U.S. Appl. No. 15/412,610, office action dated Jul. 9, 2018.
U.S. Appl. No. 15/413,257; office action dated Sep. 25, 2018.
U.S. Appl. No. 15/414,526; office action dated Nov. 16, 2018.
U.S. Appl. No. 15/414,533; office action dated Nov. 19, 2018.
U.S. Appl. No. 15/414,536; office action dated Oct. 11, 2018.
U.S. Appl. No. 15/452,669, office action dated May 5, 2017.
U.S. Appl. No. 15/452,669, office action dated Jun. 11-16, 2017.
U.S. Appl. No. 15/452,669, office action dated Nov. 26, 2018.
Arakawa et al., "Protein-Solvert Interactions in Pharmaceutica Formulations", Pharm. Res., Mar. 1991, vol. 8, Issue 3, pp. 285-291.
Armitage et al., "New approach to classifying non-Hodgkin's lymphomas: clinical features of the major histologic subtypes. Non-Hodgkin's Lymphoma Classificatian Project" J Clin Oncol 16, 2780-2795 (1998).
Asadullah et al., "Interleukin-10 therapy—review of a new approach", Pharmarcol Rev., 2003, 56(2):241-269.
Atkins et al., "High-dose recombinant interleukin-therapy in patients with metastatic melanoma: long-term survival update", Cancer J Sci Am., 2000, Suppl 6:SII-4.
Atkins, "Interleukin-2: clinical applications", Semin Oncol., 2002, 29(3 Suppl 7):12-27.
Avastin® Bevacizumab, Roche, [drug label], 24 pages, Sep. 2008.
Baba, Oleo Science 10(1):15-18 (January 2010).
Bairagi et al., Albumin: A Versatile Drug Carrier, Austin Therapeutics, (Nov. 17, 2015) vol. 2. No. 2, p. 1021 (pp. 1-6).

(56) References Cited

OTHER PUBLICATIONS

Balch et al., "The new melanoma staging system", Semin Cutan Med Surg., 2003. 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Nab-paclitaxel and bevacizumab as first-line therapy in patients with unresectable stage III and IV melanoma", J Cinical Oncology, 2009, 27, No. 15S, abstract #9071.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Bolstad et al., "A comparison of normalization methods tor high density oligonucleotide array data based on variance and bias", Bioinformatics, 19:185-193.
CAO et al., "Response of resistant melanoma to a combination of weekly paclitaxel and bevacizumab"Clin Transl Oncol, 2007, 9:119-120.
Carson et al., "A phase 2 trial of a recombinant humanized monoclonal anti-vascular endothelial growth factor (VEGF) antibody patents with malignant melanoma", Proceedings of the ASCO vol. 22, No. 2873, General Poster Session. Thirty-Ninth Annual Meeting of the American Society of Clinical Oncology, May-Jun. 3, 2003, Chicago, IL, 2 pages.
Celis, "Overlapping human leukocyte antigen class I/II binding peptide vaccine for the treatment of patients with stage IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine, Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drag Carrier Systems, 1993, 10(4), pp. 307-337.
Colman, "Effects of amino acid sequence changes on antibody-antigen interactions," Research in Immunology (145(1):33-36, (1994).
Davis, "Affinity separation ot antibody-toxin conjugate from albumin-stabilized formulation", Am Biotechnol Lab., 12(4):60-64, Mar. 1994.
Degrasse, "A Single-Stranded DNA Aptamer That Selectively Binds *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et al., "Enhanced antitumor activity and safety of albumin-bound nab-docetaxel swans polysorbate 80-based docetaxel", Eur. J. Cancer, Suppl.; 18th Symposium on molecular targets and cancer therapeutics; Prague, Czech Republic; Nov. 07-10, 2006, vol. 4, No. 12. Nov. 2006 *Nov. 2006), p. 49.
Desai et. al., "Increased antitumor activity, intratumor paclitaxel concentrations and endothelial cell transport of cremophor-free, albumin-bound paclitaxel, ABI-007, compared with cremophor-based paclitaxel", Clin Cancer Res., 2006, 12(4): 1317-24.
Deweers et al., "Daraturmumab, a novel therapeutic CD38 monoclonal antibody, Induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., Apr. 1, 2008, 31(2):173-181.
Edison, "MorphoSys," 16 pages (Aug. 8, 2013).
Elbayoumi et al., "Tumor-Targeted Nanomedicine Enhanced Antitumor Efficacy In vivo of Doxorubicin-Loaded, Long-Circulating Liposomes Modified with Cancer-Specific with Monoclonal Antibody", Clin Cancer Res., 2009, 15(6):1973-1980.
Ellyard et al., "Th2-mediated anti-tumour immunity: friend or foe?", Tissue Antigens 2007, 70(1):1-11.
Elsadek et al., "Impact of albumin on drug delivery—New applications on the horizon", J of Controlled Release, 2011, 1-25.
Elst et al. "Epidermal Growth Factor Receptor Expression and Activity in Acute Myeloid Leukemia", Blood 116:3144 (2010), abstract.
European Application No. 05743903.0, Extended European Search Report dated Jan. 24, 2011.
European Application No. 09774506.1, Extended European Search Report dated Mar. 22, 2012.
European Application No. 12781802.9, Extended Europeen Search Report dated Dec. 18, 2014.
European Application No. 13843209.1, Extended European Search Report dated Sep. 5, 2016.
European Application No. 15806443.5, Extended European Search Report dated Dec. 11, 2017.
European Application No. 15809075.3. Extended European Search Report dated Dec. 21, 2017.
Ferrara et al., "The biology of VEGF and its receptors", Nal. Med., 2003, 9:669-676.
Flaherty et al., "Final Results of E2603: a double-blind, randomized phase III trial comparing carboplatin (C)/ paclitaxel(P) with or without sorafenib(S) in metastatic melanoma", J. Clin Oncol., 2010, 28:15s (suppl; abstr 8511).
Flores et al., "Novel oral taxane therapies: recent Phase I results", Clin. Invest. vol. 3, No. 4, Apr. 1, 2013 (Apr. 1, 2013), pp. 333-341, XP055425571, UK, ISSN: 2041-6792, DOI: 10.4155/cli.13.18.
Folkman, "Angiogenesis in cancer vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendrite cells", Nat. Med., 1996, 2: 1096-1103.
Gao et al., "In vice cancer targeting and imaging with semiconductor quantum dots", Nat Biotech, 2004. 22(8):969-976.
Gogas et al., "Chemotherapy for metastatic melanoma time for a change?", Cancer, 2047, 109(3): 455-464.
Golay et al., "Mechanism of action of therapeutic monoclonal antibodies: promises and pitfalls of in vitro and in vivo assay," Arch. Biochem. Biophys. 526(2):146-153 (2012).
Graells et al., Overproduction of VEGF165 concomitantly expressed with its receptors promotes growth and survival of melanoma cells through MAPK and P13K signaling, J. Invest. Dermatol., 2004, 123:1151-1161.
Gupta et al., "Ofatumumab, the first human anti-CD20 monoclonal antibody for the treatment of B cell hematologic malignancies," Ann. N.Y. Acad. Sci., 1263, pp. 43-56 (Jul. 26, 2012).

(56) References Cited

OTHER PUBLICATIONS

Haley et al., "Nanoparticles for drug delivery in cancer treatment", Urol. Oncol: Seminars and Original Invest., 2008, 26:57-64.
Hara, "What is anti-HER2 antibody tubulin polymerization inhibitor complex T-DM1?," Pharm. Monthly 56(5):734-739 (May 2014).
Harlow et al., Antibodies: a Laboratory Manual, Cold Spring Harbor Laboratory, New York, 1988 (9 pages).
Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 386-394.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplafin and Paclitaxel as Second-Line Treatment in Patents with Unresectable Stage III or Stage IV Melanoma", Journal of Clinical Oncology, Jun. 10, 2009, vol. 27, No. 17, pp. 2823-2830.
Hegde et al. "Predictive impact of Circulating Vascular Endothelial Growth Factor Four Phase III Trials Evaluating Bevacizumab," Clinical Cancer Research, Feb. 15, 2013 (Feb. 15, 2013) vol. 19, pp. 929-937.
Hersh et al., "A Phase 2 Clinical Trial of nab-Pacitaxel in Previously Treated and Chemotherapy-Naive Patients With Metastatic Melanoma", Cancer, Jan. 1, 2010, 116:155, pp. 155-163.
Hersh et al., "A randomized, controlled phase III trial nab-Paclitaxel versus dacarbazine in chemotherapy-naive patients with metastatic melanoma", Ann Oncol, 2015, epub Sep. 26, 2015.
Hersh et al., "Open label, multicenter, phase II trial of ABI-007 in previously treated and previously untreated patients with metastatic malignant melanoma", J. Min. Oncol., 2005, 23(16S):7558 (Abstract).
Hobbs et al., "Regulation of Transport pathways in tumor vessels: of tumor type and microenvironment", Proc Natl Acad USA, Apr. 1998, 95, pp. 4607-4612.
Hodi et al., "Improved survival with Ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J Clin. Oncol., 2nd edition, Except Where melanoma', Am. J. Olin Oncol., 2002, 25:283-286.
Hood et al., Immunology, 1984, Benjamin, N.Y., 2nd edition.
Huncharek et al., "Single-agent DTIC versus combination chemotherapy with or immunotherapy in metastatic melanoma: a meta-analysis of 3273 patents from 20 randomized trials", Melanoma Research, 11:75-81, (2001).
Hunkapillar et al., "Immunology: The growing immunoglobulin gene superfamily", Nature, Sep. 1986, 323, pp. 15-16.
Huston et al., "Protein engineering of antibody binding sites: Recovery of specific activity in an anti-digoxin single-chain fv analogue produced in *Escherichia coli*", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Pacitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
International Preliminary Report on Patentability for Application No. PCT/US2008/057025, dated Sep. 15, 2009.
International Preliminary Report on Patentability for Application No. PCT/US2009/049511, dated Jan. 5, 2011.
International Preliminary Roport on Patentability for Application No. PCT/US2012/037137, dated Nov. 12, 2013.
International Preliminary Report on Patentability for Application No. PCT/US2013/062638, dated Apr. 16, 2015.
International Preliminary Report on Patentability for Application No. PCT/US2015/035505, dated Dec. 22, 2018.
International Preliminary Report on Patentability for Application No. PCT/US2015/035515, dated Dec. 29, 2016.
International Preliminary Report on Patentability for Application No. PCT/US2015/054295 dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442, dated Oct. 4, 2018.
International Preliminary Report on Patentability for Application No. PCT/US2017/023443, dated Oct. 4, 2018.
International Preliminary Report on Patentability for Application No. PCT/US2016/026287, dated Apr. 10, 2018.
International Preliminary Report on Patentability for Application PCT/US2017/017553, dated Aug. 23, 2018.
International Search Report and Written Opinion for Application No. PCT/US2008/057026, dated Jul. 1, 2008.
International Search Report and Written Opinion for Application No. PCT/US2009/049511, dated Feb. 2, 2010.
International Search Report and Written Opinion for Application No. PCT/US2012/037137, dated Sep. 28, 2012.
International Search Report and Written Opinion for Application No. PCT/US2013/062638, dated Jan. 23, 2014.
International Search Report and Written Opinion for Application No. PCT/US2015/035505, dated Nov. 24, 2015.
International Search Report and Written Opinion for Application No. PCT/US2015/035515, dated Sep. 21, 2015.
International Search Report and Written Opinion for Application No. PCT/US2015/064295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2016/047641, dated Oct. 31, 2016.
International Search Report and Written Opinion for Application No. PCT/US2017/012580, dated Mar. 17, 2017.
International Search Report and Written Opinion for Application No. PCT/US2017/017553, dated Feb. 10, 2017.
International Search Report and Written Opinion for Application No. PCT/US2017/023443, dated Jul. 16, 2017.
International Search Report and Written Opinion for Application No. PCT/US2017/023443, dated Jul. 11, 2017.
International Search Report and Written Opinion for Application No. PCT/US2017/045643, dated Oct. 25, 2017.
International Search Report and Written Opinion for Application No. PCT/US2017/050355 dated Jan. 30, 2018.
Jaime et al., "Paclitaxel antibody conjugates and trehalose for preserving the immunological activity after freeze-drying," Curr Med Chem, 2004, 11(4):439-46 Abstract Only.
Jain et al., "Delivering nanomedicine to solid tumors", Nature Reviews Clinical Oncology, Nov. 2010, 7, pp. 653-664.
Jain et al., "Normalizing tumor vasculature with anti-angiogenic therapy: a new paradigm for combination therapy," Nat. Med. 7(9):987-989 (2001).
Jain, "Normalization of tumor vasculature: an emerging concept in antiangiogenic therapy," Science 307(5706):58-62 (2005).
Jazirehi et al., "Rituximab (anti-CD20) selectively modifies Bcl-xl and apoptosis protease activating factor-1 (Apaf-1) expression and sensitizes human non-Hodgkin's-lymphoma B cell lines to paclitaxel-induced apoptosis," Mol. Cancer Ther. 2(11):1183-93 (2003).
Jiang et al., "Regulation of Immune Responses by T Cells", N Engl J Med., 2006, 354(11): 1166-1176.
Jin et al., "Paclitaxel-loaded nanoparticles decorated with anti-CD133 antibody: a targeted therapy for liver cancer stem cells," J. Nanopart. Res. 2014, 16:2157 (2014).
Jin et al. "Docetaxel-loaded PEG-albumin nanoparticles with improved antitumor efficiency against non-small cell lung cancer", Oncology Reports vol. 36, No. 2, Aug. 8, 2016 (Aug. 8, 2016), pp. 871-876, XP055425487, ISSN: 1021-335X, DOI: 10.3892/or.2016.4863.

(56) References Cited

OTHER PUBLICATIONS

Julien et al, "Utilization of monoclonal antibody-targeted nanomaterials in the treatment of cancer", 2011, MAbs. 3:467-478.

Kamat et al., "Metronomic chemotherapy enhances the efficacy of antivasculer therapy in ovarian cancer", Cancer Res., 2007, 67(1):281-288.

Kawai et al., "VEGF121 promotes lymphanglogenesis in the sentinel lymph nodes non-small cell lung carcinoma patients", Lung Cancer, 2008, 59(1):41-47.

Kelly et al. "Shape-Specific, Monodisperse Nano-Molding of Protein Particles," J. Am. Chem. Soc. 130:5438-5439 (2008).

Kikuchi et al., "Vascular endothelial growth factor and dendritic cells in human squamous cell carcinoma of the oral cavity", Anticancer Res., 2006, 26(3A):1833-1848.

Kim et al., "A dual target-directed agent against interleukin-6 receptor and tumor necrosis factor a ameliorates experimental arthritis", Scientific Rep. 6:20150 (2016).

Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncoloy: official journal of the American Society of Clinical Oncology, Jan. 1, 2012, vol. 30, No. 1, pp. 34-41.

Kirkwood et al., "A pooled analysis of eastern cooperative oncology group and intergroup trials of adjuvant high-dose interferon for melanoma", Clin Cancer Res., 2004, 10(5):1670-1677.

Kondejewski et al., "Synthesis and characterization of carbohydrate-linked murine monoclonal antibody K20-human serum albumin conjugates", Bioconjug Chem., 5(6):602-611, Nov.-Dec. 1994.

Korman et al., "Tumor immunotherapy: preclinical and clinical activity of anti-CTLA4 antibodies", Curr Opin Invest Drugs, 2005, 6(6):582-591.

Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.

Kottschade et al., "A Randomized Phase 2 Study of Temozolomide and Bevacizumab or nab-Paclitaxel, Carboplatin, and Bevacizumab in Patients with Unresectable Stage IV Melanoma",Cancer, 2013, vol. 119, issue 3, pp. 586-592.

Kratz et al., "Serum proteins as drug carriers of anticancer agents: a review"; Drug Deliv., 5(4):281-299, 1998.

Kratz, "Albumin as a drug carrier; design of prodrugs, drug conjugates and nanoparticles", J Control Release, 132(3):171-183, Epub May 17, 2006.

Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.

Kukowska-Latallo et al., "Nanoparticle Targeting of Anticancer Drug Improves Therapeutic Response in Animal Model of Human Epithelial Cancer", Cancer Res, 2005, 65(12):5317-5324.

Kumar et al., Thl/Th2 cytokine imbalance in meningioma, anaplastic astrocytoma and glioblastoma multiforme patients, Oncol. Ren., 2006, 15(6):1513-1516.

Lanzavecchia et al., "The use of hybrid hybridomas to target human cytotoxic T lymphocytes", Eur. J. Immunol., 1987, 17, pp. 105-111.

Lau et al.,"Is inhibiton of cancer angiogenesis and growth by paclitaxel schedule dependent?", Anti-Cancer Drugs, 2004, 15.871-875.

Lee et al., "The co-delivery of paclitaxel and Herceptin using cationic micellar nenoparticles", Biomaterials vol. 30, No. 5, Feb. 1, 2009, pp. 919-927.

Lei et al., "Comparing cellular uptake and cytotoxicity of targeted drug carriers in cancer cell lines with different drug resistance mechanisms", Nanomed: Nanotech, Biol, and Med., 2011, 7:324-332.

Lev et al.. "Dacarbazine causes transcriptional up-regulation of interleukin B and vascular endothelial growth factor in melanoma cells a possible escape mechanism from chemotherapy", Mol. Cancer Ther., 2003, 2:753-763.

Lev et al., "Exposure of melanoma cells to dacarbazine results in enhanced tumor growth and metastasis in vivo", J. Clin. Oncol., 2004, 22:2092-2100.

Liang et al., "IFN-alpha regulates NK cell cytotoxity through STAT1 pathway," Cytokine, Aug. 13, 2003 (Aug. 13, 2013), vol. 23, pp. 190-199.

Lin, "Salmon Calcitonin: Conformational Changes and Stabilizer Effects", AIMS Biophysics, 2015, 2(4): 695-723.

Lloyd et al. "Modelling the human immune response: performance of a 1011 human antibody repertoire against a broad panel of therapeutically relevant antigens", Protein Eng. , Design & Selection 22(3):159-168 (2009).

Lundin et al., "Phase 2 study of alemtuzumab (anti-CD52 monoclonal antibody) in patients with advanced mycosis fungoides/Sezary syndrome", Blood (2003) vol. 101, No. 11, pp. 4267-4272.

Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.

Marcoval et al., "Angiogenesis and malignant melanoma. Angiogenesis is related to the development of vertical (tumorigenic) growth phase", J. Cutan, Pathol., 1997, 24:212-218.

Markovic et al., "A phase II study of ABT-517 (thrombospondin-1 analog) for the treatment of metastatic melanoma", Am. J. Clin. Oncol., 2007, 30(3):303-309.

Markovic et al., "A reproducible method for the enumeration of functional ( cytokine producing) versus non-functional peptide-specific cytotoxic T lymphocytes in human peripheral blood", Clin. Exo. Immunol., 2006, 145:438-447.

Markovic et al., "Peptide vaccination of patients with metastatic melanoma: Improved clinical outcome in patients demonstrating effective immunization", Am J Clin Oncol., 2006, 29(4):352-360.

Matejtschuk, "Lyophilization of Proteins", Methods in Molecular Biology, Cryopreservation arid Freeze-Drying Protocols, Second Edition, Edited by: J.G. Day and G.N. Stacey, Humana Press Inc., Totowa, NJ, 2007, vol. 368, pp. 59-72.

Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.

Mayo Clinic, "Pactitaxel Albumin-Stabilized Nanoparticte Formulation and Bevacizumab in Treating Patients With Stage IV Melanoma That Cannot Be Removed by Surgery", Dec. 19, 2013, ClinicalTrials.gov., URL: https://www.clinicaltrials.gov/ct2/show/NCT02020707 (Four (4) pages).

McElroy et al., "Imaging of Primary and Metastatic Pancreatic Cancer Using a Fluorophore-Conjugated Anti-CA19-9 Antibody for Surgical Navigation", World J Surg., 2008, 32: 1057-1066.

Meadows et al. "Anti-VEGF Therapies in the Clinic," Cold Spring Harbor Perspective in Medicine, Oct. 1, 2012 (Oct. 1, 2012), vol. 2, pp. 1-27.

Melcher. "Recommendation for influenza and pneumocoocal vaccinations in people receiving chemotherapy", Clin Oncol (R Coll Radion), 2005, 17(1): 12-15.

Merchan et al., "Increased endothelial uptake of paclitaxel as a potential mechanism for its antianglogenic effects: potentiation by Cox-2 inhibition", Int. J. Cancer, 2005, 113, pp. 490-498.

Mezzaroba et al., "New potential therapeutic approach for the treatment of B-Cell malignancies using chlorambucil/Hydroxychloroquine-Loaded Anti-CD20 Nanoparticle", Sep. 2103, PLoS One vol. No. 8, Issue 9 pp. 1-10, e74216.

Middleton et al., "Randomized phase III study of temozolomide versus decarbazine in the treatment of patients with advanced metastatic malignant melanoma", J. Clin. Oncol., 2000, 18, pp. 158-166.

Miller et al., "Paclitaxel plus Bevacizumab versus Paclitaxel Alone Metastatic Breast Canoer," N Engl. J Med., (2007) vol. 357:2666-2676.

Mimura et al., Vascular endothelial growth factor inhibits the function of human mature dendritic cells mediated by VEGF receptor-2, Cancer Immunol Immunother., 2007, 56(6). pp. 761-770.

(56) References Cited

OTHER PUBLICATIONS

Mirtsching et al., "A Phase II Study of Weekly Nanopartiole Albumin-Bound Paolitaxel With or Without Trastuzumab in Metastatic Breast Cancer", Clinical Breast Cancer, 2011, 11(2):121-128.
Mocellin et al., "Cytokines and immune response in the tumor microenvironment", J Immunother., 2001, 24(5), pp. 392-407.
Motl, "Bevacizumab in combination chemotherapy for colorectal and other cancers", Am. J. Health-Svst. Pharm 2005, 62, pp. 1021-1032.
Nevala et al, "Abstract B77: Targeted nano-immune conjugates to melanoma; Preclinical testing of bevacizumab targeted nab-paclitaxel", Cancer Immunology Research, vol. 3, Oct. 1, 2015, 3 pages.
Nevala et al, "Antibody-targeted paclitaxel loaded naoparticle for the treatment of CD20 B-cell lymphoma", Scientific Reports, vol. 7, Apr. 5, 2017, 9 pages.
Nevala et al, "Antibody-Targeted Chemotherapy for the Treatment of Melanoma", Cancer Research, vol. 76, No. 13, Jul. 1, 2016, pp. 3954-3964.
Nevala et al, "Targeted nano-immune conjugates to melanoma: Preclinal testing of bevacizumab targeted nab-paclitaxel", Proceedings of the AACR Special Conference: Tumor Immunology and Immunotherapy: A New Chapter, Dec. 1, 2014, 2 pages.
NG et al., "Influence of formulation vehicle on metronomic taxane chemotherapy: albumin-bound versus cremophor EL-based paclitaxel", Clin. Cancer Res., 2006, 12, pp. 4331-4338.
Ng et al., "Taxane-mediated antiangiogenesis in vitro: influence of formulation vehicles and binding proteins", Cancer Res., 2004, 64, pp. 821-824.
Nilvebrant et al., "The Albumin-Bincling Domain as a Scaffold for Protein Engineering", Computational and Structural Biotechnology Journal, Mar. 2013, vol. 6, Issue 7, e201303099, http://dx.doi.org/10.5936/csbj.201303099.
Nishida et al, English Translation of "Clinical Trials of New Drugs Cytotoxic Effect against Multiple Myeloma with High Expression of a CD38 Antigen and a Human CD38 Monoclonal Daratumumab. CD38 Antigen", history of Medicine, Sep. 29, 2012, vol. 242, No. 13, pp. 1176-1181.
Oku et al., "Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts", Cancer Res., 1998, 58, pp. 4185-4192.
Ortaldo et al., "Effects of several species of human leukocyte interferon on cytotoxic activity o INK cells and monocytes," International Journal of Cancer, Mar. 15, 1983 (Mar. 15, 1983) vol. 31, No. 3, pp. 285-289.
Ouichi, Antibody delivery—from basics to clinical test—"Clinical development of antibody-drug conjugate," Drug Deliv. Sys. 28(5):424-429 (2013).
Parikh et al., "The vascular endothelial growth factor family and its receptors", Hematol. Oncol. Clin. N. Am., 2004, 18, pp. 951-971.
Park et al., "Anti-HER Immunoliposomes: Enhanced Efficacy Attributable to Targeted Delivery", Clin. Cancer Res., 2002, 8, pp. 1172-1181.
Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1109.
Perez et al., "Phase 2 Trial of Carboplatin, Weekly Pacitaxel, and Biweekly Bevacizumab in Patients with Unresectable Stage IV Melanoma", Cancer, 2009, vol. 115, Issue 1, pp. 119-127.
Petrelli et al., "Targeted Delivery for Breast Cancer Therapy: the History of Nanoparticle-Albtimm-Bound Paclitaxel." Expert Opinion on Pnarmacotherapy, Jun. 1, 2010 (Jun. 1, 2010), vol. 11, pp. 1413-1432.
Pikal, "Freeze-drying of proteins. Part II Formulation selection", Biopharm, 1990, 9, pp. 26-30.
Polak et al., "Mechanisms of locel Immunosuppression in cutaneous melanoma", Br J Cancer, 2007, 96(12), pp. 1879-1887.
Porrata et al., "Early lymphocyte recovery predicts superior survival after autologous hematopoletic stem cell transplantation in multiple myeloma or non-Hodgkin lymphoma", Blood, 2001, 98(3), pp. 579-585.
Porrata et al., "Timely reconstitution of immune competence affects clinical outcome following autologous stem cell transplantation", Clin Exp Med., 2004, 4(2):78-85.
Powell et al., "Adoptive transfer of vaccine-induced peripheral blood mononuclear cells to patients with metastatic melanoma following lymphodepletion", J Immunol., 2006, 177(9), pp. 6527-6539.
Pries et al., "Cytokines in bead and neck cancer", Cytokine Growth Factor Rev., 2006, 17(3), pp. 141-140.
Qu Na et al: "Cabazitaxel-loaded human serum albumin nanoparticles as a therapeutic agent prostate cancer", International Journal of Nanomedicine, vol. 11, Jul. 26, 2016 (Jul. 26, 2016), pp. 3451-3459.
Ranieri et al., "Vascular endothelial growth factor (VEGF) as a target of bevacizumab in cancer: from the biology to the clinic", Curr. Med. Chem., 2006, 13, 1845-1857.
Rao et al. "Combination of Paclitaxel and Carboplatin as Second-Line Therapy for Patients with Metastatic Melanoma", Cancer, Jan. 15, 2006, vol. 106, No. 2. pp. 375-382.
Ribas et al., "Ant-tumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen-specific CD8+ T cells in patients with melanoma", J. Immunol., 2005, 175(9), pp. 6169-6176.
Roy et al., "Tumor associated release of Interleukin-10 alters the prolactin receptor and down—regulates prolactin resposiveness of Immature cortical thymocytes", J Neuroimmunol., 2007, 186(1-2), pp. 112-120.
Rudikoff et al., "Single amino acid substitution altering antigen-binding specificity," Proc Natl Acad Sci USA 1982 vol. 79 pp. 1979-1983.
Rudnicka et al., "Rituximab causes polarization of B cells that augments its therapeutic function in NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-76.
Salven et al., "Enhanced expression of vascular endothelial growth factor in metastatic melanoma" Br. J. Cancer, 1997, 76(7), pp. 930-934.
Samaranayake et al., "Modified taxols. 5.1 Reaction of taxot with electrophilic reagents and preparation of a rearranged taxol derivative with tubulin assembly activity", J. Org. Chem., vol. 56, 1991, pp. 5114-5119.
Sandler et al., "Paclitaxel-carboplatin alone or with bevacizumab for non-small-cell lung cancer", N. Engl. J. Med., 2006, 355:2542-2550.
Sato et al., Intraepithelial CD8+tumor-infiltrating lymphocytes and a high CD8+/regulatory T cell ratio are associated with favorable prognosis in ovarian cancer, Proc Natl Acad Sci USA, 2005, 102(51):18538-10543.
Schrama et al. "Antibody targeted drugs as cancer therapeutics". Nature Reviews 5:147-159 (2006).
Sester et al., "Differences in CMV-specific T-cell levels and long-term susceptibility to CMV infection after kidney, heart and lung transplantation", Am J Transplant., 5(6):1483-1489, Jun. 2005.
Soda et al., Latest topics a new medicine "Albumin-bound paclitaxel," Mol. Respiratory Dis, 17(1):100-103 (Mar. 1, 2013).
Srivastava et al., "Angiogenesis in cutaneous melanoma: pathogenesis and clinical implications", Microsc. Res. Tech., 2003, 50:208-224.
Stancovski et al., "Mechanistic aspects of the opposing effects of monoclonal antivodies to the ERB62 receptor on tumor growth," Proc Natl Acad Sci USA, 88: 8691-8695, (1991).
Streit et al., "Angtogenesis, lymphangiogenesis, and melanoma metastasis", Oncogene, 2003, 22, pp. 3172-3179.

(56) References Cited

OTHER PUBLICATIONS

Taieb et al., "Chemoimmunotherapy of tumors: Cyclophosphamide synergtizes with exoxome based vaccines", J. Imunol., Mar. 1, 2006, 176(5):2722-2729.
Tao et al., "Inhibiting the growth of malignant melanoma by blocking the expression of vascular endothelial growth factor using an RNA interference approach", Br. J. Dermatol., 2005, 153:715-724.
Tas et al., "Circulating serum levels of angiogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 867-901.
Terui, English Translation of Molecular-Targeted Therapy for Cancer: Progresses and Challenges, "Daratumumab, Antibody Drug against Myeloma", Pharma Med., Nov. 10, 2013, vol. 31, No. 11, p. 27-30.
Ugurel et al., "Increased serum concentration of angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Vence et al., "Circulating tumor antigen-specific regulatory T cells in patients with metastatic melanoma", Proc Natl Acad Sci USA, 2007, 104(52), pp. 20884-20889.
Vishnu et al., "Safety and Efficacy of nab-Paclitaxel in the Treatment of Patients with Breast cancer," Breast Cancer: Basic and Clinical Research. 2011. vol. 5, pp. 53-65.
Volk et al., "Nab-paclitaxel efficacy in the orthotopic model of human breast cancer is significant enhanced by concurrent anti-vascular endothelial growth factor A therapy," Neoplasia 10(6):613-623 (2008).
Wagner et al., "Enhanced drug targeting by attachment of an anti alphav integrin antibody to doxorubicin loaded human serum albumin nanoparticles", Biomaterials., 31(8):2888-2398, Epub Dec. 23, 2009.
Walker et al., "Monitoring immune responses in cancer patients receiving tumor vaccines", Int Rev Immunol., 2003, 22(3-4):283-319.
Wang et al., "Biofunctionalized targeted nanoparticles for therapeutic applications". Expert Opin. Biol. Ther., 2008, 8(8): 1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-10.
Washington University School of Medicine "Phase I/II Study of Abraxene Recurrent and Refractory Lymphoma", ClinicalTrials. gov, Dec. 6, 2016, 7 pages.
Weber, "Review anti-CTLA-4 antibody ipilimumab: case studies of clinical response and Immune-related adverse events", Oncologist, Jul. 2007, 12(7), pp. 864-87.
Wiernik et al., "Phase I trial of taxol given as a 24-hour infusion every 21 days: responses observed in metastatic melanoma", Journal of Clinical Oncology, Aug. 1987, vol. 5. No. 8, pp. 1232-1239.
Wong et al., "Programmed death-1 blockade enhances expansion and functional melanoma antigen-specific: CTLs", Int. Immunol., 2007, vol. 19, No. 10, pp. 1225-1234.
Wu et al., "Aptamers: Active Targeting Ligaride for Cancer Diagnosis and therapy", Theranostics, 2015, 5(4):322-344.
Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma:

in vivo persistenoe, migration, and antitumor effect of transferred T cells", Proc Natl Acad Sci USA, 2002, 99(25):16168-16173.
Yu et al., "Interaction between bevacizumab and murine VEGF-A: a reassessment," Invest Ophthalmol. Visual Sci. 49(2): 522-527, Feb. 2008.
Yuan et al., "Vascular Permeability in a Human Tumor Xenograft: Molecular Size Dependence and Cutoff Size", Cancer Research, Sep. 1, 1995, 55, pp. 3752-3756.
Yuan et al. "Time-dependent vascular regression and permeability changes in established human tumor xenografts induced by an anti-vascolar endothelial growth factor/vascular permeability factor antibody," Proc. Natl. Acad. Sci., USA 93(25):14765-14770 (1996).
Zimpfer-Rechner et al., "Randomized phase II study of weekly pacliatxel versus paclitaxel and carboplatin as second-line therapy in disseminated melanoma: a multicentre trial of the Dermatologic Co-operative Oncology Group (DeCOG)", Melanoma Res., 2003, 13:531-536.
International Preliminary Report on Patentability for Application No. PCT/US2017/050137 dated Mar. 21, 2019.
Anonymous, "Phase I/II Study of Abraxane in Recurrent and Refractory Lymphoma", NCT01555853, CilnicalTrials, gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/225,428, office action dated Jul. 31, 2019.
U.S. Appl. No. 15/225,542; office action dated Jul. 18, 2019.
U.S. Appl. No. 15/286,024, office action dated Aug. 1, 2019.
U.S. Appl. No. 15/359,569, office action dated Jul. 26, 2019.
U.S. Appl. No. 15/412,581; office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533; office action dated Mar. 8, 2019.
U.S. Appl. No. 15/430,411, office action dated May 1, 2019.
U.S. Appl. No. 15/452,669; office action dated Jun. 24, 2019.
U.S. Appl. No. 15/456,377; office action dated Mar. 19, 2019.
U.S. Appl. No. 15/456,377; office action dated Jul. 5, 2019.
U.S. Appl. No. 15/456,382; office action dated Mar. 18, 2019.
U.S. Appl. No. 15/456,382; office action dated Jul. 8, 2019.
U.S. Appl. No. 15/456,391; office action dated Mar. 15, 2019.
U.S. Appl. No. 15/456,391; office action dated Jul. 24, 2019.
U.S. Appl. No. 15/456,391; office action dated Mar. 28, 2019.
U.S. Appl. No. 15/456,395; office action dated Aug. 14, 2019.
U.S. Appl. No. 15/456,399; office action dated Mar. 28, 2019.
U.S. Appl. No. 15/456,399; office action dated Aug. 14, 2019.
U.S. Appl. No. 15/460,552; office action dated Apr. 1, 2019 dated Aug. 14, 2019.
U.S. Appl. No. 15/460,552; office action dated Aug. 14, 2019.
U.S. Appl. No. 15/460,699; office action dated Mar. 28, 2019.
U.S. Appl. No. 15/268,288; office action dated Apr. 01, 2019.
Bedu-Addo "Understanding Lyophilization Formulation Development", Pharmaceutical Technology Lyophilization. pp. 10-18 (2004).
Beers et al. "CD20 as a Target or Therapeutic Type I and II Monoclonal Antibodies", Seminars in Hematology 47(2):107-114 (2010).
Belldegrun et al. "Human Renal Carcinoma Line Transfected with Interleukn-2 and/or Interferon alpha Gene(s): Implications for Live Cancer Vaccines", J National Cancer Institute 85(3):207-216 (1993).
Buechner "Intralesional interferon alfa-2b in the treatment of basal cell carcinoma". J Am Acad Dermatol 24:731-734 (1991).
Cheng et al. Molecularly targeted drugs for metastatic colorectal cancer, Drug Des Devel Ther. Nov. 1, 2013 ,7: 1315-22 (Year: 2013).
Coiffer "The Role of Rituximab in Lymphomas", Rev. Bras. Hematol. Hemotar., 2002, vol. 24, No. 3, ISSN: 1516-8484 (6 pages).
Doveil et al. "Adjuvant Therapy of Stage IIIb Melanoma with Interferon Alfa-2b:Clinical and Immunological Relevance", Dermatology 191:234-239 (1995).
Edwards et al. The Remarkable Flexibility of the Human Antibody Repertoire; Isolation of Over One Thousand Different Antibodies to a Single Protein, BLyS, J. Mol. Biol 334:103-118 (2003).
European Application No. 16637869.3, Extended European Search Report dated Apr. 4, 2019.

(56) References Cited

OTHER PUBLICATIONS

European Application No. 177364516, Extended European Search Report dated Jul. 8, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability Application No. PCT/US2017/050134 dated Mar. 21, 2019.
Iqbal et al, Anti-Carmen Actions of Denosumab. Curr Osteopotos Rep. Dec. 20119(4): 173-6. (Year 2011).
Khallauf et al. "5-Fluorourcil and Interferon-alpha Immunochemotherapy Enhances Immunogenicity of Murine Pancreatic Cancer Through Upregulation of NKG2D Ligands and MHC Class 1", Immunother 35(3):245-253 (2012).
Korthals et al. "Monocyte derived dendritic cells generated by IFN-alpha acquire mature dendritic and natural killer cell properties as shown by gene expression analysis", J Translated Medicine 5:46 (2007) (11 pages).
Matthey et al. Promising therapeutic targets in neuroblastoma. Clin Cancer Res. May 15, 2012;18(10):2740-53. (Year: 2012).
Package Insert, Campath® (ALEMTUZUMAB), Millennium and ILEX Partners, LP, 13 pages, available May 2001.
Reck et al. "Ipilimumab in combination with paclitaxel and carboplatin as first-line therapy in extension-disease-small-cell lung cancer results from a randomized, double-blind, multicenter phase 2 trial", Ann Oncol. 24(1):75-83 (2013).
Robak, T. Emerging monoclonal antibodies and related agents for the treatment of chronic lymphocytic leukemia. Future Oneal. Jan. 2013;9(1):69-91. Abstract Only. (Year: 2013).
Verma et al. "Effect of Surface properties on nanoparticle-cell interactions", Small, 6(1 ): 12-21, (2010).
U.S. Appl. No. 15/460,699, office action dated Aug. 28, 2019.
U.S. Appl. No. 15/461,288; office action dated Aug. 28, 2019.
U.S. Appl. No. 15/225,542; office action dated Jul. 30, 2020.
U.S. Appl. No. 15/286,024, office action dated Feb. 10, 2020.
U.S. Appl. No. 15/286,024, office action dated Jul. 29, 2020.
U.S. Appl. No. 15/359,569; office action dated Aug. 10, 2020.
U.S. Appl. No. 15/430,411, office action dated Apr. 17, 2020.
U.S. Appl. No. 15/452,669; office action dated Mar. 3, 2020.
U.S. Appl. No. 15/456,377; office action dated Mar. 12, 2020.
U.S. Appl. No. 15/456,391; office action dated Feb. 4, 2020.
U.S. Appl. No. 15/460,699; office action dated Mar. 3, 2020.
U.S. Appl. No. 15/461,288; office action dated Feb. 28, 2020.
U.S. Appl. No. 15/675,596; office action dated May 28, 2020.
U.S. Appl. No. 15/752,155; office action dated Feb. 7, 2020.
U.S. Appl. No. 16/328,146; office action dated Feb. 26, 2020.
U.S. Appl. No. 16/328,146; office action dated Jul. 28, 2020.
Barua et al. "Particle shape enhances specificity of antibody-display nanoparticles", PNAS 110(9):3270-3275 (2013).
Chuang et al. "Recombinant human serum albumin", Drugs Today 43(8):547-561 (2007) (Abstract Only) (2 pages).
European Application No. 17750912.2 Extended European Search Report dated Jan. 2, 2020.
Miele et al. "Albumin-bound formulation of paclitaxel (Abraxane® ABI-007) in the treatment of breast cancer", International Journal of Nanomedicine 4:99-105 (2009).
Warner et al. "Alemtuzumab use in relapsed and refractory chronic lymphocytic leukemia: a history and discussion of future rational use", Ther Adv Hematol 3(6):375-389 (2012).
Zhao et al. "Abraxane, the Nanoparticle Formulation of Paclitaxel Can Induce Drug Resistance by IP-Regulation of P-gp", PLoS One 10(7):e0131429 (2015) (19 pages).
Adams et al., "(P2-11-01) Safety and clinical activity of atezolizumab(anti-PDL1) in combination with nab-pacitaxel in patients with metastatic triple-negative breast cancer", 2015, XP002775314, 2015 San Antonio Breast Cancer Symposium, URL: http://sabcs.org/portals/sahcs2016/documents/sabcs-2015-abstracts.pdf?v=5

Adams et al., "Phase Ib trial of atezolizumab in combination with nab-paclitaxel in patients with metastatic triple-negative breast cancer (mTNBC)" Journal of Clinical Oncology col. 34, No. 15, May 1, 2016, 4 pages.
Anonymous, "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.
Anonymous, "Atezolizumab Plus Abraxane Promising New Treatment for Triple-Negative Breast Cancer", UNM Comprehensive Cancer Center, Jan. 7, 2016, pp. 1-2.
Emens et al.: "(OT1-01-06) A phase III randomized trial of afezolizumab in combination with nab-paclitaxel as first line therapy for patients with metastatic triple-negative breast cancer (mTNBC)", 2015, XP002775313, 2015 San Antonio Breast Cancer Symposium, URL: http://sabcs.org/portals/sabcs2016/documents/sabcs-2015-abstracts.pdf?v=5.
Fabi et al, "Prospective study on nanoparticle albumin-bound paclitaxel in advanced breast cancer: clinical results and biological observations in taxane-pretreated patients", Drug Design, Development and Therapy vol. 9, Nov. 1, 2015, 7 pages.
Hamilton et al, "Nab-Paclitaxel/Bevaczumab/Carboplatin Chemotherapy in First-Line Triple Negative Metastatic Breast Cancer, Clinical Breast Cancer", vol. 13, No. 6, Dec. 1, 2013, 6 pages.
Inman, "Atezolizumab/Nab-Paclitaxel Combo Shows High Response Rates in TNBC", OneLive, Dec. 10, 2015, 4 pages.
International Search Report and Written Opinion corresponding to International Application No. PCT/US2017/049745 dated Dec. 15, 2017.
International Search Report and Written Opinion corresponding to International Application No. PCT/US2017/049746 dated Nov. 27, 2017.
International Search Report and Written Opinion corresponding to International Application No. PCT/US2017/050134 dated Nov. 16, 2017.
International Search Report and Written Opinion corresponding to International Appl. No. PCT/US2017/050137 dated Nov. 27, 2017.
Mustacchi et al., "The role of taxanes in triple-negative breast cancer: literature review", Drug Design, Development and Therapy, vol. 9, Aug. 5, 2015, 16 pages.
Nahleh et al, "Swog S0800 (NCI COR0000636131): addition of bevacizumba to neoadjuvant nab-pacitaxel with dose-dense doxorubicin and cyclophosphamide improves pathologic complete response (pCR) rates in inflammatory or locally advanced breast cancer", Breast Cancer Research and Treatment, vol. 158, No. 3 Jul. 8, 2016, 12 pages.
Volk-Draper et al, "Novel Model for Basaloid Triple-negative Breast Cancer: Behavior In Vivo and Response to Therapy", vol. 14, No. 10, Oct. 1, 2012, 18 pages.
U.S. Appl. No. 15/752,155; office action dated Dec. 16, 2020.
"U.S. Appl. No. 15/430,411, office action dated Nov. 2, 2020".
"U.S. Appl. No. 15/452,669; office action dated Oct. 21, 2020".
"U.S. Appl. No. 15/456,377; office action dated Sep. 1, 2020".
"U.S. Appl. No. 15/675,596; office action dated Oct. 20, 2020".
"U.S. Appl. No. 16/086,977; office action dated Sep. 3, 2020".
"U.S. Appl. No. 16/330,028; office action dated Nov. 24, 2020".
Molokhia, Sarah A., et al., "The capsule drug device: Novel approach for drug delivery to the eye", Vision Research 50:680-682 (2010).
Taniwaki, L. , et al., "Effect of lyophilization on the in vitro biological activity of bevacizumab". Eye 24:1628-1629 (Jun. 25, 2010).
Anonymous "Paclitaxel Albumin-Stabilized Nanoparticle Formulation and Bevacizumab in Treating Patients With Stage IV Melanoma That Cannot Be Removed by Surgery or Gynecological Cancers", NCT02020707, ClinicalTrials.gov, Dec. 25, 2013 (13 pages).
U.S. Appl. No. 15/187,672, office action dated Sep. 11, 2019.
U.S. Appl. No. 15/225,428, office action dated Dec. 6, 2019.
U.S. Appl. No. 15/225,542, office action dated Jan. 14, 2020.
U.S. Appl. No. 15/359,569; office action dated Jan. 17, 2020.
U.S. Appl. No. 15/430,411; office action dated Oct. 31, 2019.

(56) References Cited

OTHER PUBLICATIONS

U.S. Appl. No. 15/675,596; office action dated Dec. 3, 2019.
U.S. Appl. No. 15/752,155; office action dated Sep. 25, 2019.
Cirstoiu-Hapca et al. "Benefit of anti-HER2-coated paclitaxel-loaded immuno-nanpoarticles in the treatment of disseminated ovarian cancer: Therapeutic efficacy and biodistribution in mice", Journal of Controlled Release 144:324-331 (2010).
European Application No. 17771005.0, Extended European Search Report dated Oct. 17, 2019.
European Application No. 17771006.8, Extended European Search Report dated Oct. 10, 2019.
Liu et al. "Freeze-Drying of Proteins". In: Walkers W., Oldenhof H. (eds) Cryopreservation and Freeze-Drying Protocols. Methods in Molecular Biology (Methods and Protocols), vol. 1257. Springer, New York, NY; published online Nov. 14, 2014.
Reynolds et al. "Phase II Trial of Nanoparticle Albumin-Bound Paclitaxel, Carboplatin, and Bevacizumab in First-Line Patients with Advanced Nonsquamous Non-small Cell Lung Cancer", J Thoracic Oncology 4(12):1537-1543 (2009).
Official Action in Japanese Patent Application No. 2019-512623 dated Aug. 13, 2021 (with English Translation), 14 pages.
Official Action in Mexican Patent Application No. MX/a/2019/002562 dated Oct. 12, 2021, 9 pages.

\* cited by examiner

Isotype anti-PD-L1

ABX + anti-PD-L1

Atezolizumab + anti-PD-L1

AA130 + anti-PD-L1

METHODS OF TREATING PD-L1 EXPRESSING CANCER

CROSS REFERENCE TO RELATED APPLICATIONS

This application is a 35 U.S.C. § 371 national phase application of PCT Application PCT/US2017/050137 filed Sep. 5, 2017, which claims the benefit of the priority date of U.S. Provisional Application No. 62/383,938, filed Sep. 6, 2016; the entire contents of each of which are incorporated by reference herein in its entirety.

FIELD OF THE INVENTION

This disclosure relates to novel methods and kits for treating cancer by administering nanoparticle complexes comprising a carrier protein, a binding agent that binds specifically to PD-L1, and paclitaxel. The method may also comprise pretreating a patient suffering from a cancer comprising cancer cells that express PD-L1 with anti-PD-L1 antibody alone, prior to, concurrently with or after administering the nanoparticle complexes.

STATE OF THE ART

Cancers cells employ a variety of means to escape immune surveillance and thereby continue to proliferate and/or metastasize. For example, many cancer cell types express or overexpress PD-L1 (programmed cell death ligand 1) (B7-H1), the principal ligand of program cell death protein 1 (PD-1). PD-1 is a cell surface receptor on T lymphocytes and is expressed upon activation in mature hematopoietic cells such as T and B cells, NKT cells and monocytes after prolonged antigen exposure (Ishida et al., 1992. EMBO J. 11:3887). Expression of PD-1 and PD-L1 in the tumor microenvironment appears to be a major resistance mechanism to escape immune surveillance. It is hypothesized that PD-L1 binding to PD-1 on T-cells suppresses effector anti-tumor T-cell activity and facilitates immune evasion.

There are several clinical trials that use monoclonal antibodies that either bind to PD-1 or PD-L1 in the treatment of cancers, including lung cancer, bladder cancer, kidney cancer, hematological cancers, breast cancer, colorectal cancer, melanoma and solid cancers. Anti-PD-1 antibodies known in the art include, e.g., Nivolumab (BMS-936558/MDX-1106/ONO-4538; Bristol Myers Squibb), PDR001 (Novartis), and Pembrolizumab (MK-3475) (Merck Sharp & Dohme); anti-PD-L1 antibodies known in the art include, e.g., BMS-936559/MDX-1105 (Bristol Myers Squibb), Atezolizumab (MPDL3280A, Genetech/Roche), MeDI4736 (durvalumab; MedImmune/AstraZeneca), MSB00100718C (avelumab; EMD Serono) (see, e.g., Philips and Atkins "Therapeutic uses of anti-PD-1 and anti-PD-L1 antibodies" International Immunology Vol. 27(1) pp:39-46).

Despite the antitumor activity of antibodies targeting the PD-1:PD-L1 pathway, resistance to these therapies has been increasingly observed (see, e.g., Lussier et al. J. Immunotherapy of Cancer, 2015, 3:21 and Koyama et al., Nature Communications, 2016 7:1-9 (Published online 17 Feb. 2016)). Thus there remains a need in the art to improve the efficacy of cancer therapeutics.

SUMMARY

Described herein are methods for treating a patient suffering from a cancer having cancer cells that express a programed cell death ligand 1 (PD-L1), particularly e.g., a PD-L1-expressing cancer cells that have become resistant to immunotherapy with anti-PD-L1 antibodies. The method comprises, or consists essentially of, administering, to a subject in need thereof, e.g., a mammal having cancer cells that express or overexpress PD-L1, a composition comprising a therapeutic amount of nanoparticle complexes comprising (a) a carrier protein, (b) an effective amount of a binding agent having a PD-L1 binding portion that binds to PD-L1 so as to provide directional guidance to the nanoparticle complexes to the cancer cells and (c) an effective amount of paclitaxel.

In one embodiment, the average diameter of the complexes is between 0.1 and 0.9 m. The binding agent may be an anti-PD-L1 antibody, e.g. atezolizumab. The mammal can be a human. The PD-L1-expressing cancer cells may be, e.g., melanoma, renal cell carcinoma, non-small cell lung carcinoma, head and neck squamous cell carcinoma, colorectal cancer, Merkel cell carcinoma, ovarian cancer, bladder cancer and advanced solid tumors.

The carrier protein/paclitaxel/binding agent nanoparticle complexes can be ABRAXANE®/anti-PD-L1 antibody complexes. ABRAXANE® is available from Celgene Corp. and is a nanoparticle formulation that combines paclitaxel with human albumin. The carrier protein (e.g., albumin)/paclitaxel/antibody nanoparticle complexes, or a composition comprising the complexes, can further comprise an alkylating agent. The alkylating agent can be a platinum compound. The platinum compound can be carboplatin. The anti-PD-L1 antibodies can be humanized antibodies. The anti-PD-L1 antibodies can be chimeric antibodies. The composition can be administered by injection.

In one embodiment, the PD-L1-expressing cancer cells are resistant to immunotherapy with anti-PD-L1 antibodies.

In an embodiment of the methods described herein, the complexes are administered in an amount sufficient to deliver a therapeutically effective amount of the paclitaxel.

The anti-PD-L1 antibody suitable for use in the inventions described herein includes Atezolizumab (TECENTRIQ™, Genentech, Inc. A Member of the Roche Group) or a biosimilar version thereof. In some embodiments, the anti-PD-L1 antibody is BMS-936559/MDX-1105 (Bristol Myers Squibb), Atezolizumab (MPDL3280A, Genetech/Roche), MeDI4736 (durvalumab; MedImmune/AstraZeneca), or MSB00100718C (avelumab; EMD Serono).

In an embodiment of the methods described herein, the target of the cancer cells are cells of a solid cancer.

In an embodiment of the methods described herein, the carrier protein/paclitaxel/PD-L1 binding agent nanoparticle complexes, e.g., albumin/paclitaxel/anti-PD-L1 antibody nanoparticle complexes, are lyophilized and may be reconstituted for administration to a subject in need thereof.

An embodiment of the invention includes a method for increasing the duration of uptake of a chemotherapeutic agent by a tumor that expresses PD-L1. The method includes administering the chemotherapeutic agent in a nanoparticle complex comprising a carrier protein, the chemotherapeutic agent (e.g., paclitaxel) and a PD-L1 binding agent, e.g., an antibody that specifically binds to PD-L1, wherein the binding agent provides directional guidance to the nanoparticle complex to the tumor.

As described herein, in vitro mixing of albumin-containing nanoparticles (e.g., ABRAXANE® nanoparticles) and antibodies (e.g., anti-PD-L1 antibodies, such as Atezolizumab) can result in the formation of macromolecular complexes, the characteristics of which (e.g., size, antibody content, or chemotherapeutic drug content) can be customized depending on need. In some cases, such macromolecular complexes can retain antibody mediated target binding specificity, can retain or exhibit enhanced chemotherapeutic tumor cell cytotoxicity, and can exhibit no additional toxicity beyond that of ABRAXANE® nanoparticles alone. As also described herein, contacting ABRAXANE® with an anti-PD-L1 antibody (e.g., Atezolizumab) prior to administration to a human (e.g., a human cancer patient wherein the cancer expresses or overexpresses PD-L1) can result in a complex that, when administered as a complex, has an increased ability to treat a cancer as compared to a treatment regimen that includes administering ABRAXANE® and the anti-PD-L1 antibody separately in a manner that does not form ABRAXANE®/anti-PD-L1 antibody complexes. The methods and materials provided herein can be used to increase the progression-free survival rate in cancer patients. Increasing progression-free survival can allow cancer patients to live longer. Thus the methods and materials provided herein can be used to increase the overall survival rate in cancer patients.

Also described herein are methods for treating a cancer, preferably a cancer comprising cancer cells expressing programed cell death ligand 1 (PD-L1), by administering to a patient an anti-PD-L1 antibody and nanoparticle complexes, which complexes comprise a carrier protein, paclitaxel and a binding agent that specifically binds to PD-L1, e.g., an anti-PD-L1 antibody. As described herein, the treatment of the subject having a cancer, e.g., a cancer that expresses PD-L1, or overexpresses PD-L1, with the PD-L1 antibody in combination with such nanoparticle complexes increases the therapeutic efficacy of the complexes. Preferably, such anti-PD-L1 antibodies are administered prior to treatment with such nanoparticle complexes. Accordingly, an aspect provided herein is a method for treating a patient suffering from a cancer, e.g., a cancer which expresses or overexpresses PD-L1, wherein the patient is treated with a sub-therapeutic amount of an anti-PD-L1 antibody and a therapeutic amount of nanoparticle complexes comprising the carrier, paclitaxel, and anti-PD-L1 antibody. The administration of the sub-therapeutic amount of the anti-PD-L1 antibody is such that it enhances the efficacy of the nanoparticle complexes. Without wishing to be bound by any theory, it is contemplated that administration of a sub-therapeutic amount of the anti-PD-L1 antibody enhances the therapeutic efficacy of the nanoparticle complexes by binding to non-tumor-bound PD-L1 in the body. Treatment with a sub-therapeutic amount of anti-PD-L1 antibody may allow for greater targeting of the nanoparticle complexes to the tumor, decrease the amounts of the carrier protein/paclitaxel/antibody complexes administered to a patient necessary to achieve a desired effect, or both.

In another aspect, provided herein are methods for enhancing the efficacy of carrier protein/paclitaxel/anti-PD-L1 antibody nanoparticle complexes by administering the complexes about 0.5 to 48 hours after pretreatment of a patient with a sub-therapeutic amount of anti-PD-L1 antibody. Preferably, such nanoparticle complexes are administered about 24 hours after the sub-therapeutic amount of anti-PD-L1 antibody.

In another aspect, provided herein are methods for enhancing the therapeutic outcome in a patient suffering from a cancer, e.g., a cancer expressing or overexpressing PD-L1, by treating the patient with a sub-therapeutic amount of an anti-PD-L1 antibody (e.g., an uncomplexed anti-PD-L1 antibody, e.g. not bound to a carrier protein/paclitaxel complex) and co-treating the patients with an effective amount of nanoparticle complexes comprising albumin, paclitaxel, and anti-PD-L1 antibodies wherein the complexes can bind to PD-L1. In one embodiment, the antibodies are arranged on the surface of the complexes.

In another aspect, provided herein are methods for enhancing the therapeutic outcome in a patient suffering from a cancer, e.g., a cancer expressing or overexpressing PD-L1, by treating the patient with a sub-therapeutic amount of the anti-PD-L1 antibody prior to any subsequent treatment with the nanoparticle complexes comprising carrier protein, paclitaxel, and anti-PD-L1 antibodies, wherein the complexes bind to PD-L1. In one embodiment, the antibodies are arranged on the surface of the complexes.

In an embodiment of this invention, the methods described herein are administered to a subject who has a cancer comprising cells that express PD-L1 but which cancer is resistant to immunotherapy with anti-PD-L1 antibodies that are not in complex with nanoparticles comprising a carrier protein-bound chemotherapeutic, e.g., an albumin bound-paclitaxel nanoparticle, e.g., ABRAXANE®.

Examples of cancer cells known to express PD-L1 and thus suitable for treatment with the methods disclosed herein include but are not limited to melanoma, renal cell carcinoma, non-small cell lung carcinoma, head and neck squamous cell carcinoma, colorectal cancer, Merkel cell carcinoma, ovarian cancer, bladder cancer, hematologic cancers, and other solid cancers, which cancers express PD-L1.

In an embodiment, the anti-PD-L1 antibody is atezolizumab or a biosimilar version thereof. Atezolizumab (trade name TECENTRIQ™) is a fully humanized, Fc-modified monoclonal antibody of IgG1 isotype against PD-L1. Other anti-PD-L1 antibodies include MDX-1105, a fully human monoclonal antibody that binds to PD-L; Avelumab (MSB0010718C, Merck KGaA, Darmstadt, Germany & Pfizer), a fully human monoclonal PD-L1 antibody of isotype IgG; and Durvalumab (MedImmune/AstraZeneca), an Fc optimized anti-PD-L1 mAb.

In one embodiment, the sub-therapeutic amount of anti-PD-L1 antibody is selected from an amount consisting of about 1%, about 5%, about 10%, about 15%, about 20%, about 25%, about 30%, about 35%, about 40%, about 45%, about 50%, about 55% or about 60% of the therapeutic dosage of anti-PD-L1 antibody. It is contemplated that administration of the sub-therapeutic amount of anti-PD-L1 antibody preferentially blocks circulating PD-L1 with minimal blocking of PD-L1 associated with a tumor. In some embodiments, the sub-therapeutic amount of anti-PD-L1 to be administered to the patient is determined by analyzing the level of circulating PD-L1 in the blood.

In one embodiment, the sub-therapeutic amount of anti-PD-L1 antibody is administered from between about 30 minutes to about 48 hours prior to administration of the albumin/paclitaxel/anti-PD-L1 antibody nanoparticle complexes.

In other aspects provided herein are unit-dose formulations of an anti-PD-L1 antibody, for example, atezolizumab or a biosimilar version thereof, which formulation comprises from about 1% to about 60% of a therapeutic dose of the antibody wherein the formulation is packaged so as to be administered as a unit dose.

In some embodiments, the formulation of anti-PD-L1 antibodies comprises from about 5% to about 20% of a therapeutic dose of atezolizumab or a biosimilar version thereof. The therapeutic dose for atezolizumab, e.g. for locally advanced or metastatic urothelial carcinoma, is recited in the prescribing information. The therapeutic dose is 1200 mg and preferably a subtherapeutic dose ranges from 5% to 20% of the therapeutic dose. In such a preferred embodiment, such a subtherapeutic dose would range from 60 mg to 240 mg, more preferably from 120 mg to 160 mg.

In other aspects, provided herein are kits comprising: (a) an amount of an albumin/paclitaxel/anti-PD-L1 antibody complexes, (b) a unit dose of a sub-therapeutic amount of anti-PD-L1 antibody, and optionally (c) instructions for use.

In one embodiment, the carrier-bound paclitaxel (e.g., albumin-paclitaxel, e.g., ABRAXANE®/anti-PD-L1 antibody complexes of the kits are lyophilized. The lyophilized complexes may be reconstituted in an aqueous solution prior to administration. The aqueous solution may be a sterile aqueous solution or the reconstituted aqueous solution may be filtered sterilized through e.g., a 0.2 or 0.22 μm filter.

An embodiment of the invention includes a method for increasing the duration of tumor uptake of a chemotherapeutic agent by administering the chemotherapeutic agent in a nanoparticle complex comprising a carrier protein, paclitaxel, the chemotherapeutic agent and a PD-L1 binding agent, e.g. an anti-PD-L1 antibody, the PD-L1 binding agent providing directional guidance to the nanoparticle complex to the tumor. In some embodiments, the subject receives a subtherapeutic amount of the anti-PD-L1 antibody prior to or concurrently with such nanoparticle complexes.

BRIEF DESCRIPTION OF THE DRAWINGS

The following figures are representative only of the invention and are not intended as a limitation. For the sake of consistency, nanoparticles using ABRAXANE® and atezolizumab employ the acronym "AA" and the number after AA such as AA130 is meant to confer the average particle size of these nanoparticles (in nanometers, based on Malvern Nanosight analysis).

FIG. 5B), ABX alone (45 mg/kg; FIG. 5C) and AA130 (18 mg/kg atezolizumab and 45 mg/kg ABX; FIG. 5D) one time. Tumor growth was monitored 3 times per week. Tumor size was calculated with the equation: (length× width$^2$)/2.

DETAILED DESCRIPTION

Figure 1:
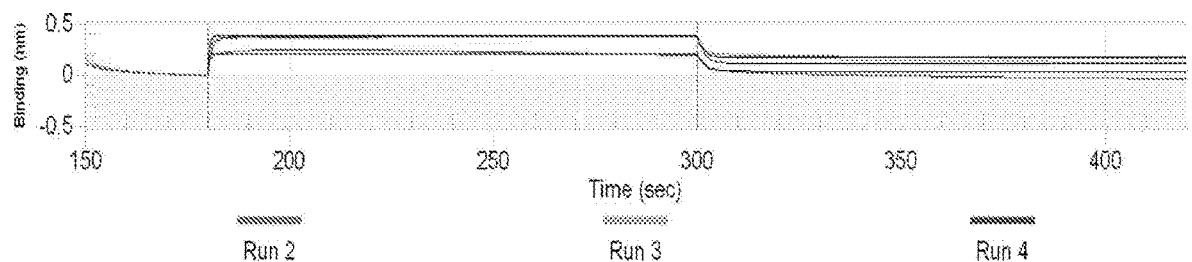
FIG. 1 shows the binding affinity between atezolizumab and ABX. The Kd was determined to be $1.462 \times 10^{-9}$. Biolayer interferometry (BLItz) (Forte Bioscience) was performed using streptavidin probes.

After reading this description it will become apparent to one skilled in the art how to implement the invention in various alternative embodiments and alternative applications.

However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "sub-therapeutic" is used to describe an amount of antibody that is below the amount of antibody conventionally used to treat a cancer. For example, a sub-therapeutic amount is an amount less than that defined by the manufacturer as being required for therapy.

The term "nanoparticle" "or "nanoparticle composition" as used herein refers to particles having at least one dimension which is less than 5 microns. In preferred embodiments, such as for intravenous administration, the particle is less than 1 micron. For direct administration, e.g., into a tumor, the particle can be larger. Even larger particles are expressly contemplated by the invention.

In a population of particles, the size of individual particles are distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50. So, for example, AA130 refers to nanoparticles having an average size of 130 nanometers (nm).

The term "nanoparticle" may also encompass discrete multimers of smaller unit nanoparticles. For example, a 320 nm particle comprises a dimer of a unit 160 nm nanoparticle. For 160 nm nanoparticles, multimers would therefore be approximately 320 nm, 480 nm, 640 nm, 800 nm, 960 nm, 1120 nm, and so on as determined by a Mastersizer 2000 (available from Malvern Instruments Ltd, Wocestershire, UK) as described in PCT/US15/54295.

The term "biosimilar" as used herein refers to a biopharmaceutical which is deemed to be comparable in quality, safety, and efficacy to a reference product marketed by an innovator company (Section 351(i) of the Public Health Service Act (42 U.S.C. 262(i)).

The term "carrier protein" as used herein refers to proteins that function to transport antibodies and/or therapeutic agents. The antibodies of the present disclosure can reversibly bind to the carrier proteins. Examples of carrier proteins are discussed in more detail below.

The term "core" as used herein refers to central or inner portion of the nanoparticle complex which may be comprised of a carrier protein, a carrier protein and a therapeutic agent, or other agents or combination of agents. In some embodiments, the antibody may be non-covalently associated (complexed) with the core.

As used herein, the term "enhancing the therapeutic outcome" and the like relative to a cancer patient refers to a slowing or diminution of the growth of cancer cells or a solid tumor, or a reduction in the total number of cancer cells or total tumor burden.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof.

As used herein, the term, "binding agent", "binding agent specific for", or "binding agent that specifically binds" refers to an agent that binds to a target antigen and does not significantly bind to unrelated compounds. Preferably the binding agent binds to the target antigen with high specificity having a dissociation constant (Kd) of $10^{-7}$ M, $10^{-8}$ M, or $10^{-9}$ M or lower. Preferably the dissociation constant is about $10^{-7}$M to about $10^{-14}$ M. Examples of binding agents that can be effectively employed in the disclosed methods include, but are not limited to, lectins, proteins, and antibodies, such as monoclonal antibodies, e.g., humanized monoclonal antibodies, chimeric antibodies, or polyclonal antibodies, or antigen-binding fragments thereof, as well as aptamers, fusion proteins, and aptamers having or fused to an albumin-binding motif. In an embodiment the binding agent is an exogenous antibody. An exogenous antibody is an antibody not naturally produced in a mammal, e.g., in a human, by the mammalian immune system.

As used herein, the term, "anti-PD-L1 binding agent", "anti-PD-L1 binding agent specific for," or "anti-PD-L1 binding agent that specifically binds" refers to an agent that binds to a PD-L1 and does not significantly bind to unrelated compounds. Preferably the PD-L1 binding agent binds to PD-L1 with high specificity having a dissociation constant of $10^{-7}$ M, $10^{-8}$ M, or $10^{-9}$ M or lower. Preferably the dissociation constant is about $10^{-7}$ M to about $10^{-14}$ M. Examples of anti-PD-L1 binding agents that can be effectively employed in the disclosed methods include, but are not limited to, antibodies, such as monoclonal antibodies, e.g., humanized monoclonal antibodies, chimeric antibodies, or polyclonal antibodies, or antigen-binding fragments thereof, as well as aptamers, fusion proteins, and aptamers. Preferably, the binding agent has or is fused to an albumin-binding motif. In an embodiment the anti-PD-L1 binding agent is an exogenous antibody.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof, including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984); Harlow and Lane, Antibodies. A Laboratory Manual, Cold Spring Harbor Laboratory (1988); Hunkapiller and Hood, Nature, 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. In an embodiment the antibody is an exogenous antibody. An exogenous antibody is an antibody not naturally produced in a mammal, e.g., in a human, by the mammalian immune system.

The term "dissociation constant," also referred to as "Kd," refers to a quantity expressing the extent to which a particular substance separates into individual components (e.g., the protein carrier, antibody, and/or therapeutic agent).

The terms "lyophilized," "lyophilization" and the like as used herein refer to a process by which the material (e.g., nanoparticles) to be dried is first frozen and then the ice or frozen solvent is removed by sublimation in a vacuum environment. An excipient is optionally included in prelyophilized formulations to enhance stability of the lyophilized product upon storage. In some embodiments, the nanoparticle complexes can be formed from lyophilized components (carrier protein, antibody and therapeutic) prior to use as a therapeutic. In other embodiments, the carrier protein, antibody, and therapeutic agent are first combined into nanoparticle complexes and then lyophilized. The lyophilized sample may further contain additional excipients.

The term "buffer" encompasses those agents which maintain the solution pH in an acceptable range prior to lyophilization and may include succinate (sodium or potassium), histidine, phosphate (sodium or potassium), Tris(tris (hydroxymethyl)aminomethane), diethanolamine, citrate (sodium) and the like. In some embodiments, the buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

The term "reconstitution time" is the time that is required to rehydrate a lyophilized formulation into a solution.

A "stable" formulation is one in which the protein therein essentially retains its physical stability and/or chemical stability and/or biological activity upon storage.

The term "epitope" as used herein refers to the portion of an antigen which is recognized by an antibody. Epitopes include, but are not limited to, a short amino acid sequence or peptide (optionally glycosylated or otherwise modified) enabling a specific interaction with a protein (e.g., an antibody) or ligand. For example, an epitope may be a part of a molecule to which the antigen-binding site of an antibody attaches.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. In some embodiments "treating" or "treatment" refers to the killing of cancer cells.

The term "kill" with respect to a cancer treatment is directed to include any type of manipulation that will lead to the death of that cancer cell or at least a portion of a population of cancer cells.

The term "dose" refers to an amount of the antibody or nanoparticle complex given to a patient in need thereof. The attending clinician will select an appropriate dose from a range based, e.g., on the patient's weight, age, health, stage of cancer, level of circulating PD-L1, and other relevant factors, all of which are well within the skill of the art.

The term "unit dose" refers to a dose of the antibody or nanoparticle complex that is given to the patient to provide a desired result. In some instances, the unit dose is sold in a sub-therapeutic formulation (e.g., 10% the therapeutic dose). The unit dose may be administered as a single dose or a series of subdoses. The therapeutic dose for an antibody for a given FDA-approved indication is recited in the prescribing information, for example the therapeutic dose of Atezolizumab, which is approved for the treatment of patients with locally advanced or metastatic urothelial carcinoma, is 1200 mg administered as an intravenous infusion over 60 or 30 minutes every 3 weeks until disease progression or unacceptable toxicity, and preferably a subtherapeutic dose ranges from 5% to 20% of the therapeutic dose. In such a preferred embodiment such a subtherapeutic dose would range from 60 mg/kg to 240 mg/kg, more preferably from 120 mg/kg to 180 mg/kg. The therapeutic dose for an antibody for a given indication where the antibody is not yet FDA approved or the antibody is not yet approved for that indication, will be the amount the correlates to the therapeutic dose that has been approved for other indications, and thus the subtherapeutic dose for the non-FDA approved indications is readily calculated as a percent of the therapeutic dose (e.g., 10% of the therapeutic dose). For example, the therapeutic dose and therefore the subtherapeutic dose of an antibody for the treatment of metastatic melanoma correlates to the therapeutic dose for metastatic cancers in general that has been approved.

Additionally, some terms used in this specification are more specifically defined below.

Overview

As will be apparent to the skilled artisan upon reading this disclosure, the present disclosure relates to methods for treating a patient having cancer cells that express PD-L1, and particularly cancer cells that are or have become resistant to treatment with anti-PD-L1 antibody immunotherapy, by treating the patient with carrier protein/paclitaxel/anti-PD-L1 antibody nanoparticle complexes containing a therapeutically effective amount of the paclitaxel.

The present disclosure also relates to methods for treating a patient having cancer cells that express PD-L1, and particularly cancer cells that are or have become resistant to treatment with anti-PD-L1 antibody immunotherapy, by treating the patient with a sub-therapeutic amount of an anti-PD-L1 antibody and carrier protein/paclitaxel/anti-PD-L1 antibody nanoparticle complexes containing a therapeutically effective amount of the paclitaxel.

Anti-PD-L1 Antibodies

In some embodiments, the anti-PD-L1 antibody is atezolizumab or a biosimilar version thereof.

Atezolizumab (TECENTRIQ™, Roche, USA) is a fully humanized, Fc-modified monoclonal antibody of IgG1 isotype against PD-L1. Atezolizumab is a PD-L1 blocking antibody has been approved for the treatment of patients with locally advanced or metastatic urothelial carcinoma (including bladder cancer) and non-small cell lung cancer.

Other anti-PD-L1 antibodies are also known in the art, e.g., BMS-936559/MDX-1105 (Bristol Myers Squibb), MeDI4736 (Durvalumab, MedImmune/AstraZeneca), and MSB00100718C (avelumab, EMD Serono).

In some embodiments, the sub-therapeutic amount of anti-PD-L1 antibody is selected from an amount consisting of about 1%, about 5%, about 10%, about 15%, about 20%, about 25%, about 30%, about 35%, about 40%, about 45%, about 50%, about 55% or about 60% of the therapeutic dosage of anti-PD-L1 antibody.

In some embodiments, the sub-therapeutic amount of anti-PD-L1 antibody is an amount which preferentially blocks circulating PD-L1 without blocking PD-L1 associated with the tumor.

Complexes

Methods suitable for preparing carrier protein/paclitaxel/anti-PD-L1 antibody, complexes are described, for example, in U.S. Provisional App. No. 62/060,484, filed Oct. 6, 2014; and U.S. Provisional Patent Application Nos. 62/206,770; 62/206,771; and 62/206,772 filed Aug. 18, 2015, as well as PCT Publication Nos. WO2016/057554, filed Oct. 6, 2015; and WO2014/055415, filed Sep. 30, 2013. The contents of each of these applications are specifically incorporated by reference in their entireties. Example 1 below provides one example of a detailed protocol for making such complexes.

The nanoparticle complexes that may be used in the methods described herein may also comprise a PD-L1 binding agent other than an anti-PD-L1 antibody. Such PD-L1 binding agent comprises a PD-L1 binding portion and an albumin-binding motif, wherein the PD-L1 binding agent complexes with a nanoparticle of carrier protein-bound chemotherapeutic, e.g., an albumin bound paclitaxel nanoparticle, e.g., ABRAXANE®, forming a nanoparticle complex that retains the ability to bind to PD-L1, e.g., after lyophilization and reconstitution. For example that PD-L1 binding agent may be a PD-L1-binding aptamer having or fused to an albumin-binding motif, etc.

In some embodiments, the anti-PD-L1 antibody is atezolizumab or a biosimilar version thereof. In some embodiments, the antibodies are a substantially single layer of antibodies on all or part of the surface of the nanoparticle. In some embodiments the nanoparticle complexes comprise between about 100 and 1000 antibodies, or between about 400 and about 800 antibodies.

In some embodiments the carrier protein is albumin, e.g., a human serum albumin. In some embodiments that albumin is a recombinant human serum albumin.

In some embodiments, the complexes further comprise at least one additional chemotherapeutic agent, e.g., a chemotherapeutic agent selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

In some embodiments, the carrier-bound chemotherapeutic is an albumin-bound paclitaxel, e.g., ABRAXANE® (Celgene).

In one embodiment, the antibodies of the nanoparticle complexes are integrated onto and/or into the nanoparticle complexes, e.g. on the surface of an albumin-bound paclitaxel core. In one embodiment, the antibodies of the nanoparticle complexes are arranged on a surface of the carrier protein (e.g., albumin)-bound paclitaxel core. In one embodiment, the antibodies of the nanoparticle complexes are associated with the albumin-bound paclitaxel core. In one embodiment, the antibodies of the nanoparticle complexes are non-covalently associated with (bound to) a carrier protein, e.g. albumin, in the nanoparticle complex. In one embodiment, the carrier protein (e.g., albumin) and paclitaxel are associated (bound to each other) via non-covalent bonds.

In some embodiments of the invention, the composition comprising the nanoparticle complexes may further comprise an additional chemotherapeutic agent. The additional chemotherapeutic agent may be e.g., an alkylating agent, e.g., a platinum compound, e.g., carboplatin.

In some embodiments, the nanoparticle complex sizes are between 0.09 m to 0.9 m, between 90 nm and 800 nm, including about 90 nm, 100 nm, 130 nm, 160 nm, 200 nm, 300 nm, 400 nm, 500 nm, 600 nm, 700 nm or 800 nm. In some embodiments, the nanoparticle complex sizes are between about 100 nm and about 225 nm. In other embodiments, the nanoparticle complexes are larger, e.g., from greater than 800 nm to about 3.5 µm. In some embodiments, the particles are multimers of nanoparticle complexes. In some embodiments the nanoparticle complexes have average particle sizes of about 100 nm to about 225 nm, either freshly made or after lyophilization and resuspension in an aqueous solution suitable for injection.

Without being bound by theory, the binding agent is believed to be bound by the carrier protein through hydrophobic interactions, which, by their nature, are weak. Yet the activity of the individual components, as well as their relative relationship in the nanoparticle are preserved despite lyophilization and reconstitution of the composition. It is still further contemplated that binding to the carrier protein, e.g., complexation of the binding agent to the carrier protein, occurs through an albumin binding motif on the binding agent, and/or an antibody-binding motif on the carrier protein. Albumin-binding motifs and antibody-binding motifs are described in PCT Application No. PCT/US17/45643, filed Aug. 4, 2017, which is incorporated herein by reference in its entirety. In some embodiments, the binding agent is a non-therapeutic and non-endogenous human antibody, a fusion protein, e.g., fusion of an antibody Fc domain to a peptide that binds a target antigen, or an aptamer.

Treatment Methods

In one aspect is provided a method for treating a patient having a cancer which expresses PD-L1, the method comprising administering to the patient a therapeutically effective amount of anti-PD-L1/albumin/paclitaxel nanoparticles to treat the cancer. In one embodiment, the method comprises selecting a patient having a cancer which expresses PD-L1. In one embodiment, the method comprises selecting a patient having a cancer which expresses PD-L1 and is resistant to treatment with a checkpoint inhibitor immunotherapy. In one embodiment, the checkpoint inhibitor immunotherapy comprises anti-PD-L1 antibodies that are not part of a nanoparticle complex as described herein.

In one aspect is provided a method for treating a patient in need thereof, wherein the patient is treated with a sub-therapeutic amount of an anti-PD-L1 antibody and albumin/paclitaxel/anti-PD-L1 antibody nanoparticle complexes containing a therapeutically effective amount of paclitaxel, such that the administration of the sub-therapeutic amount of the anti-PD-L1 antibody enhances the efficacy of the nanoparticle complexes. A subject in need thereof may be a subject afflicted with a cancer wherein the cancer cells express or over express PD-L1. The subject may also be afflicted with a cancer wherein the cancer cells express or over express PD-L1 but are resistant to treatment with an anti-PD-L1 antibody immunotherapy. In one embodiment, the sub-therapeutic amount of anti-PD-L1 antibodies is not in a nanoparticle complex comprising a carrier protein (e.g., albumin) bound chemotherapeutic ("uncomplexed" anti-PD-L1 antibody).

In one embodiment, the method comprises selecting a patient having a cancer wherein the cancer cells express or over express PD-L1. In one embodiment, the method comprises selecting a patient having a cancer wherein the cancer cells express or over-express PD-L1 but are resistant to treatment with an anti-PD-L1 antibody immunotherapy. Methods are known in the art for determining whether a tumor comprises cancer cells expressing PD-L1, e.g., the Ventana PD-L1(sp263) Assay (Roche), which was approved by the FDA as a complementary diagnostic to provide PD-L1 status on patients with metastatic urothelial cancer, and the PD-L1 IHC 28-8 pharmDx assay (Dako, Agilent Pathology Solutions).

In some embodiments of this invention, the nanoparticle complexes comprise a PD-L1 binding agent other than an anti-PD-L1 antibody. In some embodiments of this invention, the nanoparticle complexes comprise an anti-PD-L1 antibody that is the same antibody as the "uncomplexed" anti-PD-L1 antibody. In some embodiments of this invention, the nanoparticle complexes comprise an anti-PD-L1 antibody that is a different antibody than the "uncomplexed" anti-PD-L1 antibody.

The patient may be co-treated with a sub-therapeutic amount of an anti-PD-L1 antibody and carrier protein (e.g., albumin)/paclitaxel/anti-PD-L1 antibody nanoparticle complex.

For the sake of clarification, "co-treatment" refers to treatment of the cancer expressing PD-L1 with an anti-PD-L1 antibody prior to, concurrently with, or immediately after administration of the carrier (e.g., albumin)/paclitaxel/anti-PD-L1 antibody nanoparticle complexes, such that the anti-PD-L1 antibody is capable of binding circulating PD-L1.

In one embodiment, the anti-PD-L1 antibody is administered in a sub-therapeutic dose prior to administration of the nanoparticle complexes. In this embodiment, the administration of the anti-PD-L1 antibody occurs about 0.5 hours to about 48 hours prior to administration of the nanoparticle complexes.

In another embodiment, the anti-PD-L1 antibody composition is administered between 0.5 hours prior to and up to 0.5 hours after administration of the nanoparticle complexes. In this embodiment, it is contemplated that such administration will nevertheless result in binding of some of the circulating PD-L1 by the antibody.

In yet another embodiment, the antibody composition can be administered up to 2 hours post administration of the nanoparticle complexes.

In a preferred aspect, there is provided methods for enhancing the efficacy of albumin/paclitaxel/anti-PD-L1 antibody nanoparticle complexes by administering the albumin/paclitaxel/anti-PD-L1 antibody nanoparticle complexes about 0.5 hours to 48 hours after pretreatment of a patient with a sub-therapeutic amount of anti-PD-L1 antibody. Preferably, such nanoparticle complexes are administered about 24 hours after the sub-therapeutic amount of anti-PD-L1 antibody.

In another aspect, there is provided methods for enhancing the therapeutic outcome in a patient suffering from a cancer expressing PD-L1 which patient is selected to be treated with nanoparticles comprising albumin, paclitaxel and anti-PD-L1 antibodies, which method comprises treating the patient with a sub-therapeutic amount of the anti-PD-L1 antibody prior to any subsequent treatment with the nanoparticles.

In another aspect, there is provided methods for enhancing the therapeutic outcome in a patient suffering from a cancer overexpressing PD-L1, the method comprising co-treating the patient with a sub-therapeutic amount of the anti-PD-L1 antibody and with an effective amount of nanoparticle complexes comprising albumin-bound paclitaxel and anti-PD-L1 antibodies.

In another aspect, there is provided a method for enhancing the therapeutic outcome in a patient suffering from a cancer expressing PD-L1, which patient is to be treated with nanoparticle complexes comprising albumin, paclitaxel and anti-PD-L1 antibodies, which method comprises treating the patient with a sub-therapeutic amount of the anti-PD-L1 antibody within +/−0.5 hours of administration of the nanoparticles.

In another aspect is provided a method for enhancing the therapeutic outcome in a patient suffering from a cancer overexpressing PD-L1 which patient has been treated with a sub-therapeutic amount of the anti-PD-L1 antibody, the method comprising treating the patients with an effective amount of nanoparticles comprising albumin-bound paclitaxel and anti-PD-L1 antibodies within +/−0.5 hours of administration of the antibodies.

In some embodiments the anti-PD-L1 antibody is administered prior to the carrier protein (e.g., albumin)/paclitaxel/anti-PD-L1 antibody complex, for example, the anti-PD-L1 antibody can be administered minutes, hours or days prior to administration of the carrier protein (e.g., albumin)/paclitaxel/anti-PD-L1 antibody complex. In some embodiments, the anti-PD-L1 antibody is administered between about 5 to about 59 minutes, about 10 to about 50 minutes, about 15 to about 45 minutes, about 20 to about 40 minutes, about 25 to about 35 minutes prior to administration of the carrier protein (e.g., albumin)/paclitaxel/anti-PD-L1 antibody nanoparticle complex. In other embodiments, the anti-PD-L1 antibody can be administered about 1 hour, about 2 hours, about 3 hours, about 4 hours, about 5 hours, about 6 hours, about 12 hours, about 24 hours, about 48 hours, about 72 hours, or longer prior to administration of the carrier protein (e.g., albumin)/paclitaxel/anti-PD-L1 antibody complex. In other embodiments, the anti-PD-L1 antibody can be administered about 1 day, about 2 days, about 3 days, about 4 days, about 5 days, about 6 days, about 7 days, about 10 days, about 12 days, about 15 days, or longer prior to administration of the carrier protein (e.g., albumin)/paclitaxel/anti-PD-L1 antibody complex. Contemplated values include any value, subrange, or range within any of the recited ranges or values, including endpoints.

In some embodiments, the anti-PD-L1 antibody can be administered concurrently with administration of the carrier protein (e.g., albumin)/paclitaxel/anti-PD-L1 antibody complex, for example, within 10 minutes or less of each other.

In other embodiments, the anti-PD-L1 antibody can be administered subsequent to administration of the albumin/paclitaxel/anti-PD-L1 antibody complex, for example, within 2 hours after administration of the albumin/paclitaxel/anti-PD-L1 antibody complex.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, nonseminoma[teratomas, choriocarcinomas]), stromal tumors and germ cell tumors; thyroid cancer, including thyroid adenocarcinoma and medullar carcinoma; and renal cancer including adenocarcinoma and Wilms tumor. Cancers suitable for treatment with the methods described herein include but are not limited to cancers that express or overexpress PD-L1. Cancers that may be treated with the methods disclosed herein also include cancers that are resistant to treatment with anti-PD-L1 antibody immunotherapy, including cancers that had been responsive to immunotherapy but developed resistance to the anti-PD-L1 antibody immunotherapy, which anti-PD-L1 antibodies are not in complex with a nanoparticle comprising a carrier protein (e.g., albumin)-bound chemotherapeutic (e.g., ABRAXANE®).

Antibody Formulations

In one aspect, the anti-PD-L1 antibody is a unit-dose formulation of an anti-PD-L1 antibody which formulation comprises from about 1% to about 60% of a therapeutic dose of the antibody, wherein the formulation is packaged so as to be administered as a unit dose. In an aspect of the invention, the unit-dose formulation of an anti-PD-L1 antibody comprises about 10% of a therapeutic dose of the antibody. For example 10% of a therapeutic dose of an anti-PD-L1 antibody, e.g., atezolizumab, may be 60 mg to 240 mg.

The unit-dose formulation of an anti-PD-L1 antibody can be about 1% to about 60%, about 5% to about 50%, about 10% to about 40%, about 15% to about 30%, about 20% to about 25%, of a therapeutic dose of the anti-PD-L1 antibody. Contemplated values include any value, subrange, or range within any of the recited ranges, including endpoints.

In some embodiments, the anti-PD-L1 antibody is atezolizumab or a biosimilar version thereof, which formulation comprises from about 5% to about 20% of a therapeutic dose of atezolizumab or a biosimilar version thereof.

In another aspect, provided herein is a formulation comprising an anti-PD-L1 antibody provided herein, and at least one pharmaceutically acceptable excipient.

In general, the unit-dose formulations provided herein can be formulated for administration to a patient by any of the accepted modes of administration. Various formulations and drug delivery systems are available in the art. See, e.g., Remington's Pharmaceutical Sciences, edited by E. W. Martin (Mack Publishing Company, 18th ed., 1990).

In general, unit-dose formulations provided herein will be administered as pharmaceutical compositions by any one of the following routes: oral, systemic (e.g., transdermal, intranasal or by suppository), or parenteral (e.g., intramuscular, intravenous or subcutaneous) administration.

The unit-dose formulations may be comprised of, in general, an anti-PD-L1 antibody, optionally in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Nanoparticle Complex Formulations

In one aspect, the composition comprising the nanoparticle complexes described herein is formulated for systemic delivery, e.g., intravenous administration.

In one aspect, the nanoparticle composition is formulated for direct injection into a tumor. Direct injection includes injection into or proximal to a tumor site, perfusion into a tumor, and the like. Because the nanoparticle composition is not administered systemically, a nanoparticle composition formulated for direct injection into a tumor may comprise any average particle size. Without being bound by theory, it is believed that larger particles (e.g., greater than 500 nm, greater than 1 µm, and the like) are more likely to be immobilized within the tumor, thereby providing what is believed to be a better beneficial effect.

In another aspect, provided herein is a composition comprising a compound provided herein, and at least one pharmaceutically acceptable excipient.

In general, the compounds provided herein can be formulated for administration to a patient by any of the accepted modes of administration. Various formulations and drug delivery systems are available in the art. See, e.g., Gennaro, A. R., ed. (1995) Remington's Pharmaceutical Sciences, 18th ed., Mack Publishing Co.

In general, compounds provided herein will be administered as pharmaceutical compositions by any one of the following routes: oral, systemic (e.g., transdermal, intranasal or by suppository), or parenteral (e.g., intramuscular, intravenous or subcutaneous) administration.

The formulations described herein may include excipients. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present formulations may, if desired, be presented in a pack or dispenser device containing a unit-dose of the active ingredient. Such a pack or device may, for example, comprise metal or plastic foil, such as a blister pack, or glass, and rubber stoppers such as in vials. The pack or dispenser device may be accompanied by instructions for administration. Compositions comprising a unit-dose formulation of the invention formulated in a compatible pharmaceutical carrier may also be prepared, placed in an appropriate container, and labeled for treatment of an indicated condition.

Kits

In some aspects, the current invention relates to kits comprising: (a) an amount of albumin-/paclitaxel/anti-PD-L1 antibody nanoparticle complexes, (b) a unit dose of a sub-therapeutic amount of anti-PD-L1 antibody, and optionally (c) instructions for use.

In some embodiments, the kits can include lyophilized complexes of the albumin/paclitaxel/anti-PD-L1 antibody.

In some preferred embodiments, the kit components can be configured in such a way that the components are accessed in their order of use. For example, in some aspects the kit can be configured such that upon opening or being accessed by a user, the first component available is the unit dose of a sub-therapeutic amount of anti-PD-L1 antibody, for example, in a first vial. A second container (e.g., a vial) comprising or containing an amount of the albumin/paclitaxel/anti-PD-L1 antibody nanoparticle complexes can then be accessed. As such the kits can be intuitively configured in a way such that the first vial must be opened prior to the second vial being opened. It should be understood that in some embodiments, the order can be different, for example, where it is desired to administer the complex first, prior to the administration of the antibody. Also, it can be configured such that both are administered at the same time. Finally, it should be understood that additional vials or containers of either or both component(s) can be included, and configured for opening in any desired order. For example, the first vial could be antibody, the second vial could include complex, a third could include either antibody or complex, etc. It is contemplated that a kit configured in such a way would prevent, or at least help to prevent, the components from being administered in an order not intended by the instructions for use.

In some aspects, the invention is directed to a kit of parts for administration of albumin/paclitaxel/anti-PD-L1 antibody complexes and a unit dose of a sub-therapeutic amount of anti-PD-L1 antibody; and optionally further comprising a dosing treatment schedule in a readable medium. In some embodiments, the dosing schedule includes the sub-therapeutic amount of anti-PD-L1 antibody required to achieve a desired average serum level is provided. In some embodiments, the kit of parts includes a dosing schedule that provides an attending clinician the ability to select a dosing regimen of the sub-therapeutic amount of anti-PD-L1 antibody based on the sex of the patient, mass of the patient, and the serum level that the clinician desires to achieve. In some embodiments, the dosing treatment is based on the level of circulating PD-L1 in the blood of the patient. In some embodiments, the dosing schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

EXAMPLES

The present disclosure is illustrated using a pre-treatment of atezolizumab (i.e., TECENTRIQ™) followed by nanoparticles composed of albumin-bound paclitaxel (i.e., ABRAXANE®) and atezolizumab (i.e., TECENTRIQ™).

One skilled in the art would understand that making and using the nanoparticles, as well as administration of a co-treatment of atezolizumab, of the Examples are for the sole purpose of illustration, and that the present disclosure is not limited by this illustration.

Any abbreviation used herein, has normal scientific meaning. All temperatures are ° C. unless otherwise stated. Herein, the following terms have the following meanings unless otherwise defined:

| ABX | = | ABRAXANE ®/(albumin-bound paclitaxel) |
| --- | --- | --- |
| ATZ | = | atezolizumab |
| BSA | = | bovine serum albumin |
| kg | = | kilogram |
| nM | = | nano molar |
| mg | = | milligram |
| ml or mL | = | milliliter |
| m$^2$ | = | square meters |
| mm$^3$ | = | cubic millimeter |
| µg | = | microgram |
| µl | = | microliter |
| µm | = | micrometer/micron |
| PBS | = | Phosphate buffered saline |

Example 1: Making Atezolizumab-ABRAXANE® Nanoparticles

Atezolizumab and ABRAXANE® (ABX) were co-incubated at room temperature for 30 minutes at a concentration of 4 mg/mL and 10 mg/mL, respectively to form the nanoparticle, AA130.

To determine whether atezolizumab and ABX are capable of interacting to form nanoparticle complexes, Biolayer interferometry (BLItz) (Forte Bioscience) was performed using streptavidin probes. 100 ug/ml of biotinylated atezolizumab in 1×PBS was bound to the streptavidin probe. After washing unbound atezolizumab from the probe, the antibody-bound probe was exposed to ABX at concentrations of 100, 500, 1000 µg/mL in 1×PBS. An antibody probe exposed to PBS was used as background and background was subtracted. BLItz software was used to calculate dissociation constants (FIG. 1). The Kd was determined to be $1.462 \times 10^{-9}$.

Example 2: Size Determination of Atezolizumab-ABRAXANE® Nanoparticles

Mastersizer NS300 was employed to determine the particle size of atezolizumab bound ABX relative to ABX alone. Nanosight uses dynamic light scattering and Brownian motion to calculate particle size.

Figure 2A:
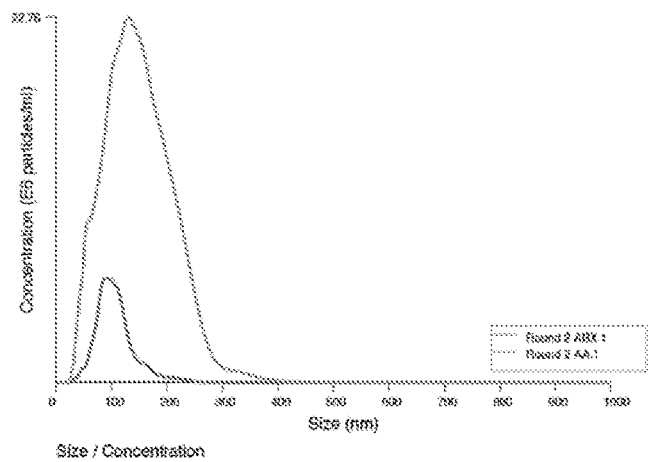
FIG. 2A shows the particle size distribution for ABX alone (average size of 90 nm) and ABX-atezolizumab nanoparticles (AA; average size of 129 nm), as determined by Mastersizer NS300.
Figure 2B:
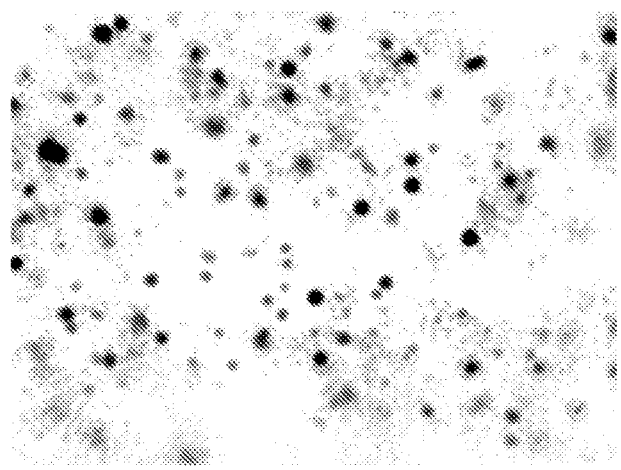
FIG. 2B is a photograph of the ABX-atezolizumab nanoparticles from FIG. 8A.

Atezolizumab and ABX were co-incubated to form the nanoparticle, AA130, as described above. ABX was diluted 1:200 and atezolizumab-bound ABX was diluted 1:800; three 30-second video clips were captured and analyzed to determine particle size (FIG. 2A). FIG. 2B is a still image from one of the video clips of AA130. The average particle size of the atezolizumab-ABX nanoparticles was determined to be about 129 nm; average size of ABX alone is about 90 nm.

Example 3: AA130 Binds PD-L1

Flow cytometry was performed to access binding of atezolizumab and atezolizumab bound Abraxane to the ligand, PD-L1. The PD-L1 positive melanoma cell line, C8161 was used for this experiment. AA130 was made as described above and an aliquot of the nanoparticles was spun at 6000 rpm for 10 minutes to remove any unbound atezolizumab. C8161 cells were stained with FITC labeled isotype control and anti-human PD-L1 as negative and positive controls, respectively. The C8161 cells were incubated for 30 minutes with ABX and atezolizumab alone and the AA130 nanoparticle. After the incubation the cells were labeled with FITC labeled anti-human PD-L1 for 30 minutes and washed with FACS buffer (1×PBS+0.5% BSA and 0.05% Na azide). After washing, the cells were analyzed by flow cytometer on the Guava 8HT and data analysis performed with Gauvasoft software (Millipore).

Figure 3A:
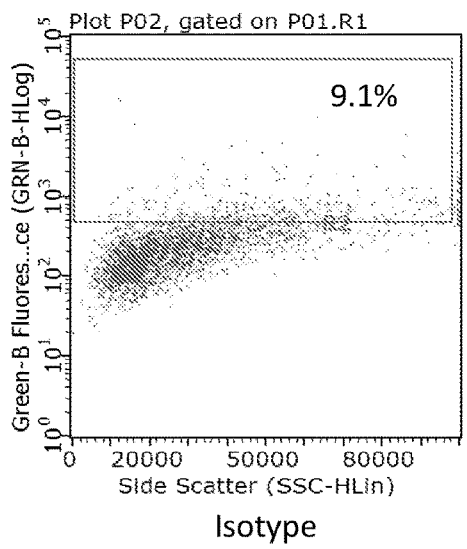
FIGS. 3A-3E show flow cytometry of ABX-atezolizumab nanoparticles (AA130) competing with labeled anti-PD-L1 antibody for binding to a PD-L1 positive human melanoma cell line, C8161. C8161 cells were pre-treated with isotype control antibody (FIG. 3A), no treatment (FIG. 3B), ABRAXANE® (FIG. 3C), atezolizumab (FIG. 3D), or AA130 (FIG. 3E), then labeled with fluorescently-labeled anti-PD-L1 antibody.
Figure 3B:
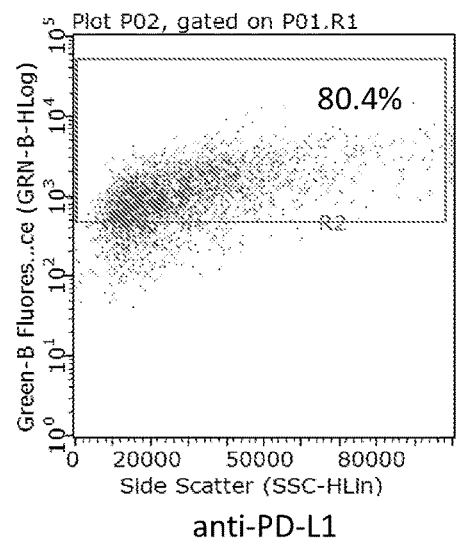
Figure 3C:
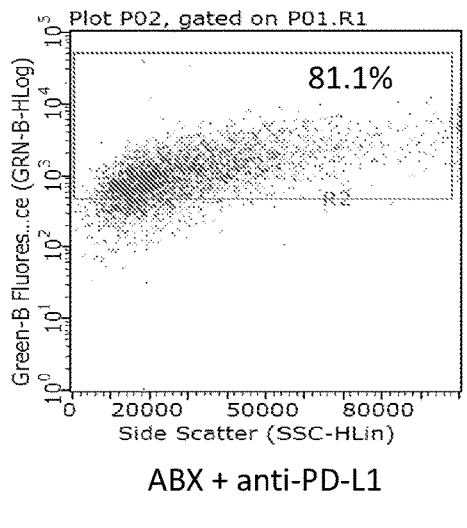
Figure 3D:
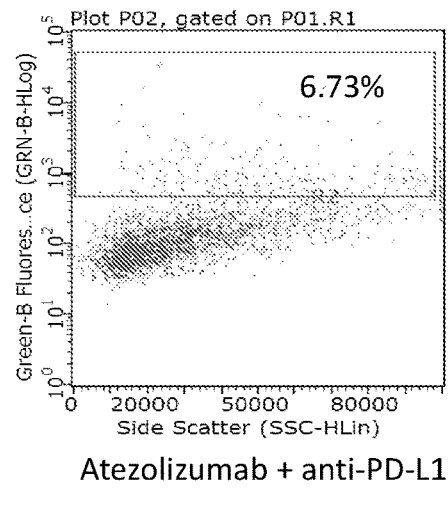
Figure 3E:
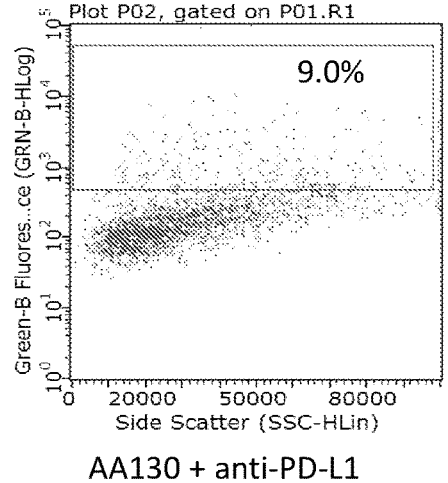

C8161 cells were pre-treated with isotype control antibody (FIG. 3A), no treatment (FIG. 3B), ABRAXANE® (FIG. 3C), atezolizumab (FIG. 3D), or AA130 (FIG. 3E), then labeled with fluorescently-labeled anti-PD-L1 antibody. The atezolizumab in the context of the 130 nm particle retains its ability to bind its ligand, PD-L1.

Example 4: AA130 Cellular Toxicity

C8161 melanoma cells were exposed to ABX and AA130 at paclitaxel concentrations from 0 to 200 µg/mL overnight to determine cell toxicity. The cells were also incubated with EdU, a thymidine analog. The next day the cells were harvested, fixed with 2% paraformaldehyde and permeabolized with 1% saponin. After permeabolization the cells were incubated for 30 minutes with a FITC labeled anti-EdU antibody to determine the percentage of cells proliferating. After washing, the cells were analyzed by flow cytometer on the Guava 8HT and data analysis performed with Gauvasoft software (Millipore). The proliferation index was calculated by normalization to an untreated positive control.

Figure 4:
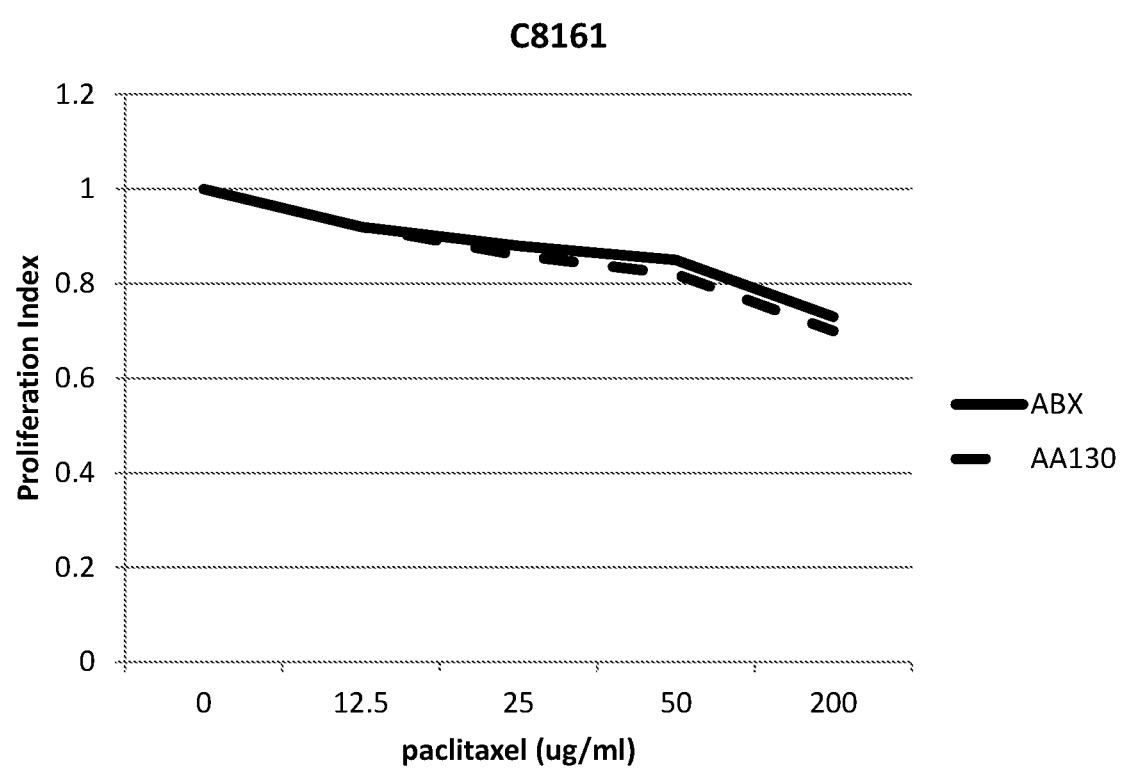
FIG. 4 shows the dose-dependent toxicity of ABX (solid line) and AA130 (broken line) on C8161 cells.
Figure 5A:
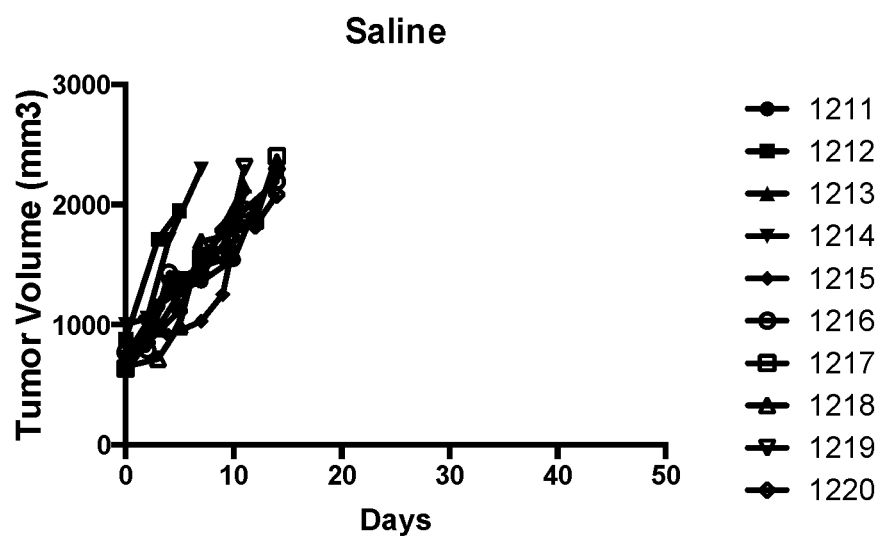
FIGS. 5A-5D show the change in tumor volume over time in mice that were injected with $2 \times 10^6$ PD-L1 positive C8161 melanoma tumor cells, then treated by 100 ul IV tail vein injection with saline (FIG. 5A), atezolizumab alone (18 mg/kg.
Figure 5B:
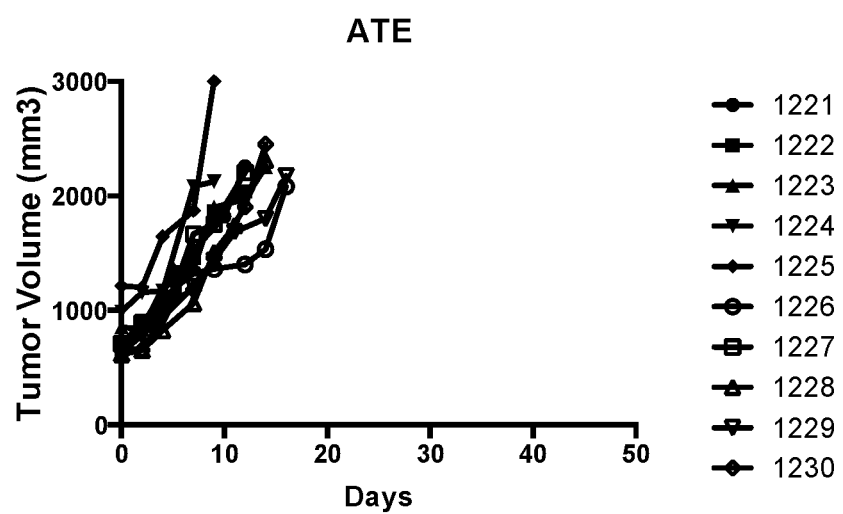
Figure 5C:
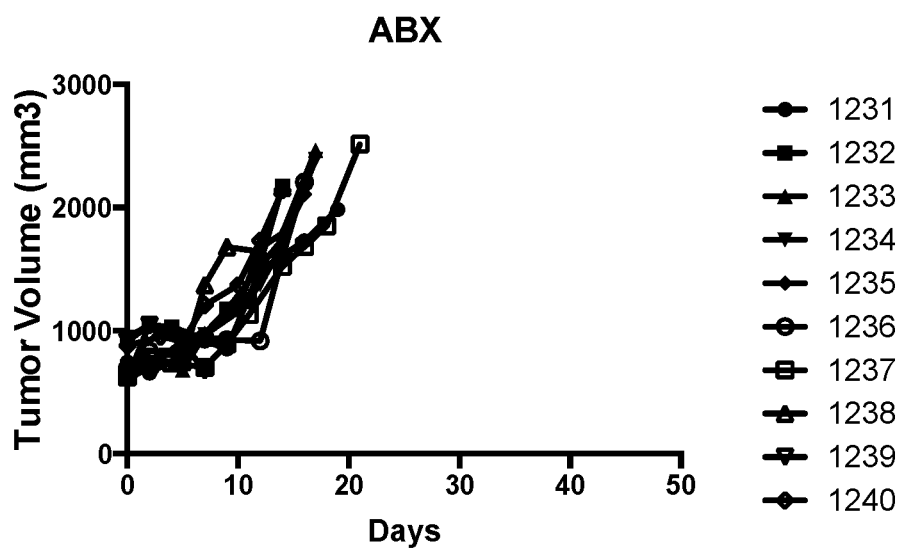
Figure 5D:
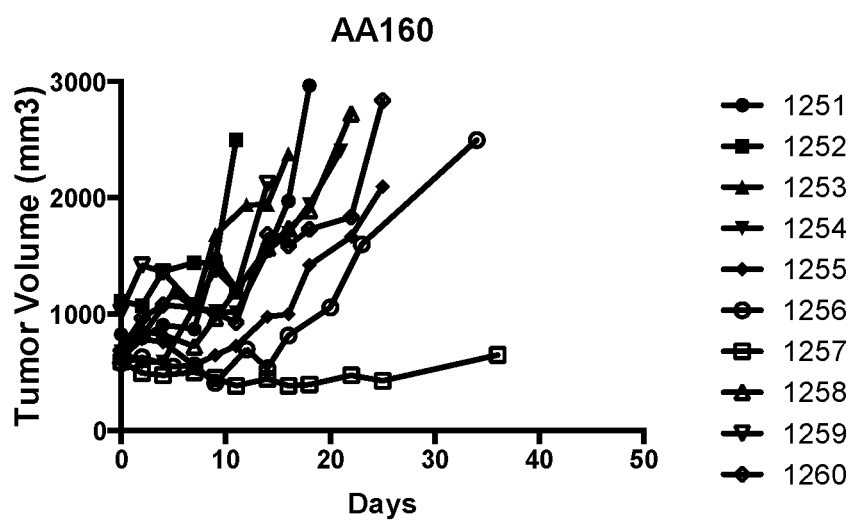

FIG. 4 shows the dose-dependent toxicity of ABX (solid line) and AA130 (broken line) on C8161 cells. The AA130 nanoparticle complex has cellular toxicity similar to ABX alone.

Example 5: Making of Intravenous Formulation of AA130 Nanoparticle Complexes For use in humans, the AA130 complexes are prepared by obtaining the dose appropriate number of 4 mL vials of 25 mg/mL ATZ and diluting each vial per the following directions to 4 mg/mL. The dose appropriate number of 100 mg vials of ABX is prepared by reconstituting to a final concentration containing 10 mg/mL ABX nanoparticles. Using a sterile 3 mL syringe, 1.6 mL (40 mg) of atezolizumab (25 mg/mL) is withdrawn and slowly injected, over a minimum of 1 minute, onto the inside wall of each of the vials containing 100 mg of ABX. The atezolizumab solution should not be injected directly onto the lyophilized cake as this will result in foaming. Then, using a sterile 12 mL sterile syringe, 8.4 mL 0.9% Sodium Chloride Injection, USP, is withdrawn and slowly injected, over a minimum of 1 minute, 8.4 mL onto the inside wall of each vial containing ABX 100 mg and ATZ 40 mg. Once the addition of ATZ 1.6 mL and 0.9% Sodium Chloride Injection, USP 8.4 mL is completed, each vial is gently swirled and/or inverted slowly for at least 2 minutes until complete dissolution of any cake/powder occurs. Generation of foam should be avoided. At this point, the concentration of each vial should be 100 mg/10 mL ABX and 40 mg/10 mL ATZ. The vials containing the ABX and ATZ should sit for 60 minutes. The vial(s) is gently swirled and/or inverted every 10 minutes to continue to mix the complex. After 60 minutes has elapsed, the calculated dosing volume of ABX and ATZ is withdrawn from each vial and is slowly added to an empty viaflex bag. An equal volume of 0.9% Sodium Chloride Injection, USP is then added to make the final concentration of ABX 5 mg/mL and ATZ 2 mg/mL. The bag is then be gently swirled and/or inverted slowly for 1 minute to mix. The ABX:ATZ nanoparticles are stored for up to 4 hours at room temperature following final dilution.

Example 6: Co-Treatment with ATZ Improves Targeting of ABX/ATZ Complexes

Athymic nude mice are injected with $1 \times 10^6$ A375 human melanoma cells in the right flank and then are treated with PBS, 12 mg/kg ATZ, 30 mg/kg ABX, AA130, or pretreated with 1.2 mg/kg ATZ and, 24 hr later, AA130. AA130 are prepared as described in PCT Application No. PCT/US15/54295 and Example 1 above. It is contemplated that only mice treated with AA130 (with or without pretreatment with ATZ) will show reduction in average tumor volume.

It is also contemplated that pretreatment with ATZ will be associated with a statistically significant reduction in tumor volume over control or ATZ alone, or ABX alone.

Tumors are measured on day 15 following treatment with either saline (PBS), TECENTRIQ™ (ATZ), ABRAXANE® (ABX), AA130, or a pretreatment of ATZ one day before AA130 (ATZ+AA130). A 10% sub-therapeutic dose of ATZ, as compared to the dose give to the ATZ alone or AA130 cohort, is given to the ATZ+AA130 cohort 24 hours prior to administration of the AA130. It is contemplated that the ATZ+AA130 cohort will present with delayed tumor growth, even when compared to AA130. It is contemplated that these experiments will show that pre-treatment with ATZ+AA130, increases survival.

Survival is again assessed at day 40. It is contemplated that median survival of mice treated with ATZ pretreatment and AA130 will exceed median survival or the mice treated with either PBS or ATZ alone.

Example 7: Fluorescence Over Time of AlexaFluor 750 Labeled Nanoparticles

Mice are injected IV with equal amounts of either labeled ABRAXANE®, or nanoparticles of ABRAXANE® having surface complexation with atezolizumab (ATZ) as per Example 1 above (AA130); one AA130 group of mice receives a pre-treatment of 1.2 mg/kg atezolizumab. Fluorescent imagery is performed at an excitation/emission spectrum of 710/760. Regions of interest (ROI) in the mice are assigned by software to track tumor accumulation based on a fluorescence threshold. Fluorescence per unit area of background ROIs and tumor ROIs for all three treatment groups is determined at 24, 29, and 48 hours post injection The amount of fluorescence (and thus paclitaxel) in the tumor and background ROIs at 24, 29 and 48 hour are determined and it is contemplated that the data will demonstrate that pretreatment with ATZ results in higher levels of tumor fluorescence as compared AA130 alone or ABRAXANE alone. It is contemplated that pretreatment with ATZ and use of ABRAXANE® nanoparticles having surface complexation with ATZ provides for a method for increasing the duration of tumor uptake of albumin containing a chemotherapeutic agent both at 24 hours and 48 hours. It is also contemplated that use of ABRAXANE® nanoparticles having surface complexation with ATZ also provides for increasing the duration of tumor uptake of these albumin containing nanoparticles with or without pretreatment with ATZ at 48 hours.

Without being limited to any theory, the antibody coating of the albumin nanoparticles imparts stability possibly by reducing liver or kidney clearance and/or by reducing protease degradation of the albumin carrier.

Example 8: In Vivo Efficacy of AA130 Nanoparticles

Athymic nude mice (Harlan Sprague Dawley) were injected with 2×10$^6$ PD-L1 positive C8161 melanoma tumor cells. The tumors were allowed to grow until about 600 mm$^3$ and were treated by 100 µl IV tail vein injection with saline, atezolizumab alone (18 mg/kg), ABX alone (45 mg/kg) and AA130 (18 mg/kg atezolizumab and 45 mg/kg ABX) one time (FIGS. 5A-5D). Tumor growth was monitored 3 times/week. Tumor size was calculated with the equation: (length× width$^2$)/2.

Figure 6:
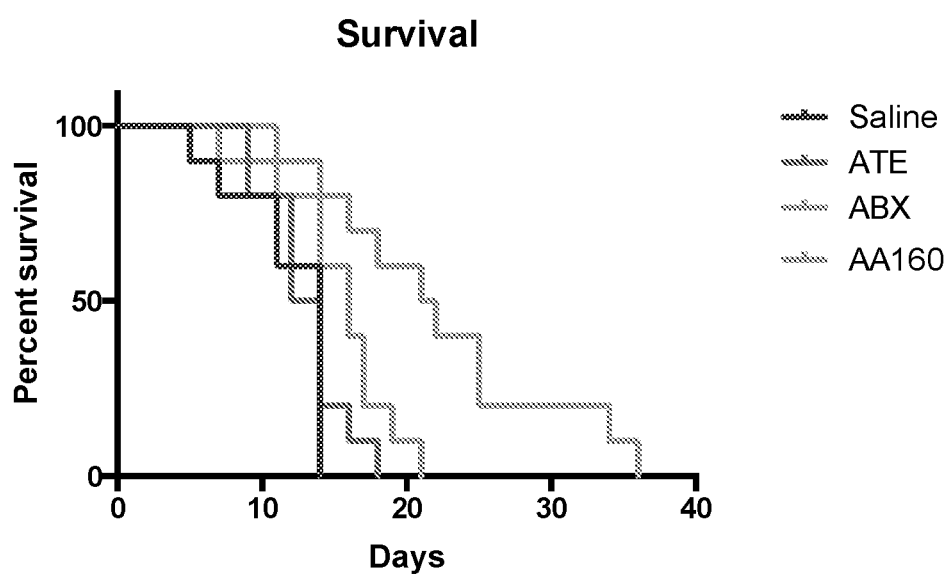
FIG. 6 depicts the survival of the mice from the experiment shown in FIGS. 11A-11D. Kaplan Meier curves were generated using Graph Pad software. The median survival for each group was 14, 13, 16, and 21.5 days for saline, atezolizumab, Abraxane and AA130, respectively. Survival differences between AA130 and all other groups were significant, with p-values of 0.0008 for saline, 0.0015 for atezolizumab, and 0.0113 for ABX.

Tumor growth curves (FIG. 6) show slowed tumor growth in the mice treated with AA130 relative to saline and the individual drugs alone. Kaplan Meier curves were generated using Graph Pad software. The median survival for each group was 14, 13, 16, and 21.5 days for saline, atezolizumab, ABX and AA130, respectively. Survival differences between AA130 and all other groups were significant with p-values of 0.0008 for saline, 0.0015 for atezolizumab, and 0.0113 for Abraxane.

What is claimed is:

1. A method for treating a patient suffering from a cancer which comprises cells expressing PD-L1, the method comprising treating said patient with a sub-therapeutic amount of an uncomplexed anti-PD-L1 antibody and nanoparticle complexes comprising (a) albumin, (b) an effective amount of an anti-PD-L1 antibody, and (c) paclitaxel.

2. The method of claim 1, wherein the amount of anti-PD-L1 antibody is effective to provide directional guidance to the nanoparticle complexes to the cancer cells.

3. The method of claim 1, wherein the cancer cells are resistant to immunotherapy comprising uncomplexed anti-PD-L1 antibodies which are not complexed with a nanoparticle comprising a carrier protein and paclitaxel.

4. The method of claim 1, wherein the nanoparticle complexes comprise an additional chemotherapeutic agent.

5. The method of claim 1, wherein the anti-PD-L1 antibody is atezolizumab or a biosimilar version thereof.

6. The method of claim 1, wherein the sub-therapeutic amount of the uncomplexed anti-PD-L1 antibody is selected from an amount consisting of about 1%, about 5%, about 10%, about 15%, about 20%, about 25%, about 30%, about 35%, about 40%, about 45%, about 50%, about 55% or about 60% of the therapeutic dosage of anti-PD-L1 antibody.

7. The method of claim 1, wherein the sub-therapeutic amount of the uncomplexed anti-PD-L1 antibody is administered from between about 30 minutes to about 48 hours prior to administration of the nanoparticle complexes.

* * * * *